US012728537B2

(12) United States Patent
Noohi Bezanjani et al.

(10) Patent No.: US 12,728,537 B2
(45) Date of Patent: Sep. 8, 2026

(54) TEMPORAL NON-OVERLAP OF TELEOPERATION AND HEADREST ADJUSTMENT IN A COMPUTER-ASSISTED TELEOPERATION SYSTEM

(71) Applicant: Intuitive Surgical Operations, Inc., Sunnyvale, CA (US)

(72) Inventors: Ehsan Noohi Bezanjani, Los Gatos, CA (US); Olga Greenberg, San Jose, CA (US); Mohammad Sina Parastegari, Campbell, CA (US); Russell Parrish, San Jose, CA (US); Maureen Riddell, San Jose, CA (US); Charles A. Sweeney, Manteca, CA (US); Allen C. Thompson, Los Altos, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 57 days.

(21) Appl. No.: 18/840,876

(22) PCT Filed: Mar. 16, 2023

(86) PCT No.: PCT/US2023/015390

§ 371 (c)(1),
(2) Date: Aug. 22, 2024

(87) PCT Pub. No.: WO2023/177802

PCT Pub. Date: Sep. 21, 2023

(65) Prior Publication Data

US 2025/0162157 A1 May 22, 2025

Related U.S. Application Data

(60) Provisional application No. 63/320,962, filed on Mar. 17, 2022.

(51) Int. Cl.
*B25J 9/16* (2006.01)
*A47C 7/38* (2006.01)
*A61B 34/35* (2016.01)

(52) U.S. Cl.
CPC ............... *B25J 9/1689* (2013.01); *A47C 7/38* (2013.01); *A61B 34/35* (2016.02)

(58) Field of Classification Search
CPC .......... B25J 9/1689; A47C 7/38; A61B 34/35; A61B 2090/065; A61B 90/60; A61B 2034/742; A61B 34/74; A61B 34/37
See application file for complete search history.

(56) References Cited

U.S. PATENT DOCUMENTS 5,876,325 A 3/1999 Mizuno et al.
6,424,885 B1 7/2002 Niemeyer et al.
(Continued)

FOREIGN PATENT DOCUMENTS

WO WO-2021041249 A1 3/2021
WO WO-2021041253 A1 3/2021
WO WO-2023014732 A1 2/2023

OTHER PUBLICATIONS

International Search Report and Written Opinion for Application No. PCT/US2023/015390, mailed Jun. 30, 2023, 22 pages.
(Continued)

*Primary Examiner* — Dylan M Katz
(74) *Attorney, Agent, or Firm* — Patterson + Sheridan, LLP

(57) ABSTRACT

A computer-assisted teleoperation system and method for operating the same are provided that enforce a temporal non-overlap of a teleoperation of a follower device and a physical adjustment of a headrest of the computer-assisted teleoperation system.

24 Claims, 6 Drawing Sheets

(56) References Cited

U.S. PATENT DOCUMENTS

| | | | | |
|---|---|---|---|---|
| 8,808,164 | B2 | 8/2014 | Hoffman et al. | |
| 9,179,832 | B2 | 11/2015 | Diolaiti | |
| 10,653,486 | B2 | 5/2020 | Ishihara et al. | |
| 2016/0183930 | A1 | 6/2016 | Herzlinger et al. | |
| 2018/0092706 | A1* | 4/2018 | Anderson | G06F 3/013 |
| 2020/0015598 | A1 | 1/2020 | Hondori et al. | |
| 2020/0100852 | A1 | 4/2020 | Ishihara et al. | |
| 2020/0261160 | A1 | 8/2020 | Peine et al. | |
| 2020/0360096 | A1* | 11/2020 | Savall | A61B 34/25 |

OTHER PUBLICATIONS

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

International Preliminary Report on Patentability for Application No. PCT/US2023/015390, mailed Sep. 26, 2024, 14 pages.

* cited by examiner

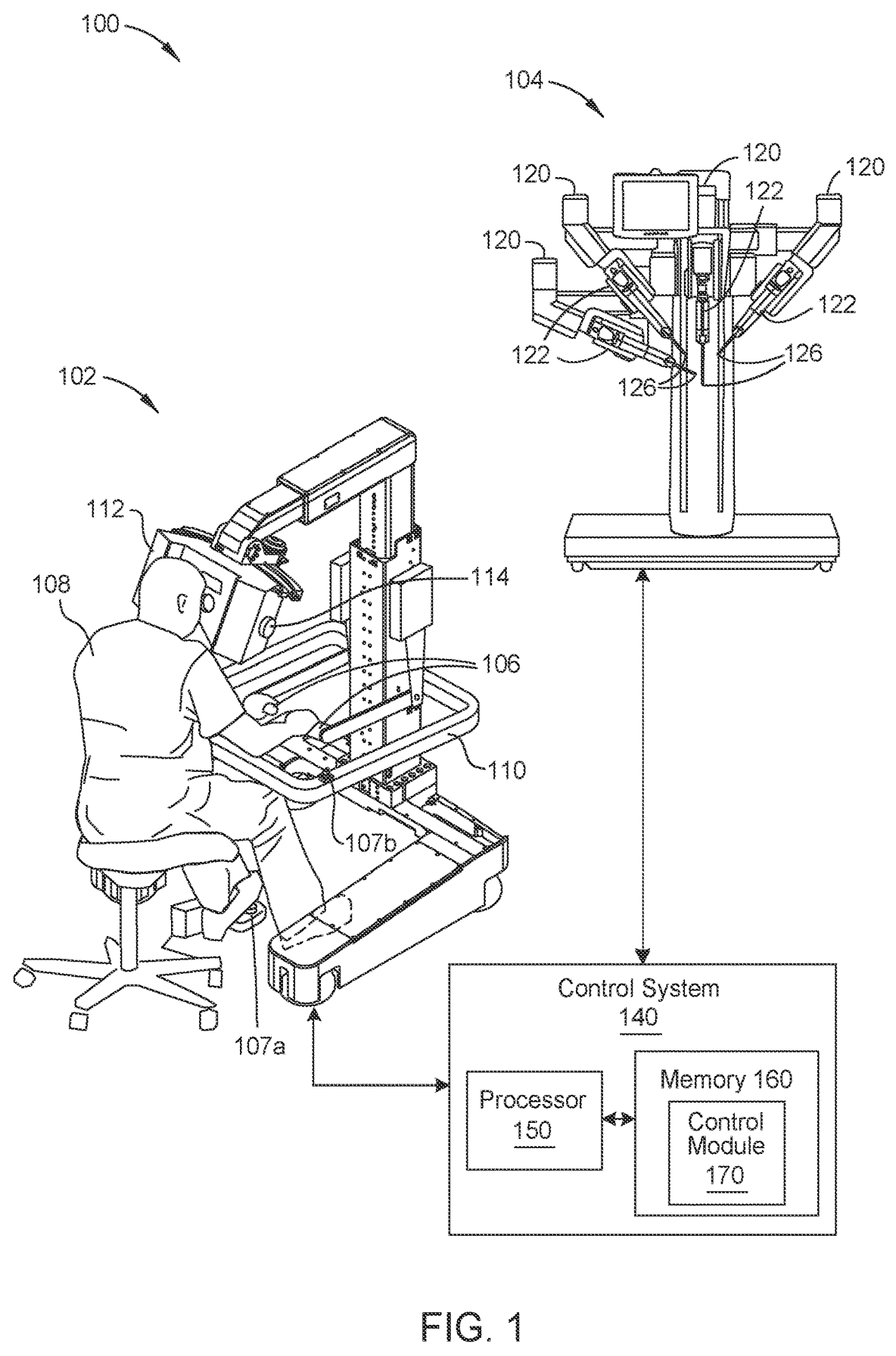

100

104

120 120 120 120

122 122 122 122

126 126

102

112

114

108

106

110

107b

107a

Control System
140

Processor
150

Memory 160

Control
Module
170

FIG. 1

TEMPORAL NON-OVERLAP OF TELEOPERATION AND HEADREST ADJUSTMENT IN A COMPUTER-ASSISTED TELEOPERATION SYSTEM

TECHNICAL FIELD

The present disclosure relates generally to electronic devices and more particularly to preventing temporal non-overlap of teleoperation and physical adjustment of headrest in a computer-assisted teleoperation system.

BACKGROUND

Computer-assisted electronic devices are being used more and more often. This is especially true in industrial, entertainment, educational, and other settings. As a medical example, the medical facilities of today have large arrays of electronic devices being found in operating rooms, interventional suites, intensive care wards, emergency rooms, and/or the like. Many of these electronic devices may be capable of autonomous or semi-autonomous motion. It is also known for personnel to control through teleoperation the motion and/or operation of electronic devices using one or more input devices. As a specific example, minimally invasive, robotic telesurgical systems permit operators who are surgeons to operate on patients from bedside or remotely. Telesurgery refers generally to surgery performed using surgical systems where the surgeon uses some form of remote control, such as a servomechanism, to manipulate surgical instrument movements rather than directly holding and moving the instruments by hand.

When an electronic device is used to perform a task at a worksite, one or more imaging devices (e.g., endoscopes, ultrasonic probes, etc.) can capture images of the worksite that provide visual feedback to an operator who is monitoring and/or performing the task. The imaging device(s) may be controllable to update a view of the worksite that is provided, such as by using a display unit, to the operator. The display unit may have lenses and/or view screens.

To use the display unit, the operator positions his or her head so as to see images displayed on one or more view screens directly or through one or more intervening components. However, when the head is positioned at a less optimal position relative to the images, the operator may have a less optimal view of the images being displayed. Example effects of less optimal views of images include the operator being unable to see an entire displayed image, seeing stereoscopic images that do not properly fuse, etc. Additionally, while using the electronic device, the operator may position their head in a manner that creates fatigue or discomfort. As a result, the operator may experience frustration, neck and/or eye fatigue, inaccurate depictions of the items in the images, etc. These and other issues, and any urge of the operator to mitigate these issues, could impact of the operation of the electronic device.

Accordingly, there is a need for improved techniques for managing system adjustment, such as headrest adjustment, in an electronic device.

SUMMARY

A computer-assisted teleoperation system and method for operating the same are disclosed herein that enforce temporal non-overlap of (i) teleoperation of a follower device in response to operator input received at an operator input device, and (ii) a physical adjustment to a headrest.

In one example, a computer-assisted teleoperation system is provided that includes an input device, a display unit, a headrest, and a control system. The input device is configured to receive operator's inputs from an operator. The display unit is configured to display images viewable by the operator. The headrest is coupled to the display unit and is configured to be contacted by a head of the operator (even though some operators may choose not to contact the headrest configured to be thus contacted). The control system is communicatively coupled to the input device. The control system includes one or more processors. The control system is configured to enforce a temporal non-overlap of (i) a teleoperation of a follower device in response to the operator input received at the input device, and (ii) a physical adjustment to the headrest.

In another example, a computer-assisted teleoperation system is provided that includes an input device, a display unit, a headrest, and a control system. The input device is configured to receive operator inputs from an operator. The display unit is configured to display images viewable by the operator. The headrest is coupled to the display unit and is configured to be contacted by a head of the operator. The control system is communicatively coupled to the input device. The control system includes one or more processors. The control system is configured to enforce a temporal non-overlap of a teleoperation mode of the control system and a headrest adjustment mode of the control system. The control system is further configured to, while in the teleoperation mode, process an input received at the input device as a teleoperation command for the computer-assisted teleoperation system, and not command the headrest actuator to move the headrest relative to the display unit in response to a headrest command input. The control system is also further configured to, while in the headrest adjustment mode, not process the input received at the input device as the teleoperation command, and command the headrest actuator to move the headrest relative to the display unit in response to the headrest command input.

In another example, a method for operating a computer-assisted teleoperation system that includes an input device configured to receive inputs from an operator, a display unit configured to display images viewable by the operator, a headrest coupled to the display unit, and a control system comprising one or more processor. The method includes receiving, by the control system, an operator input at the input device to teleoperate a follower device; and enforcing, by the control system, a temporal non-overlap of a teleoperation of a follower device in response to the operator input received at the input device and a physical adjustment to the headrest.

Other embodiments include, without limitation, one or more non-transitory machine-readable media including a plurality of machine-readable instructions which when executed by one or more processors are adapted to cause the one or more processors to perform any off the methods disclosed herein.

The foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

FIG. 1 is a simplified diagram including an example of a computer-assisted device in the form of a teleoperated system, according to various embodiments.

DETAILED DESCRIPTION

Figure 2:
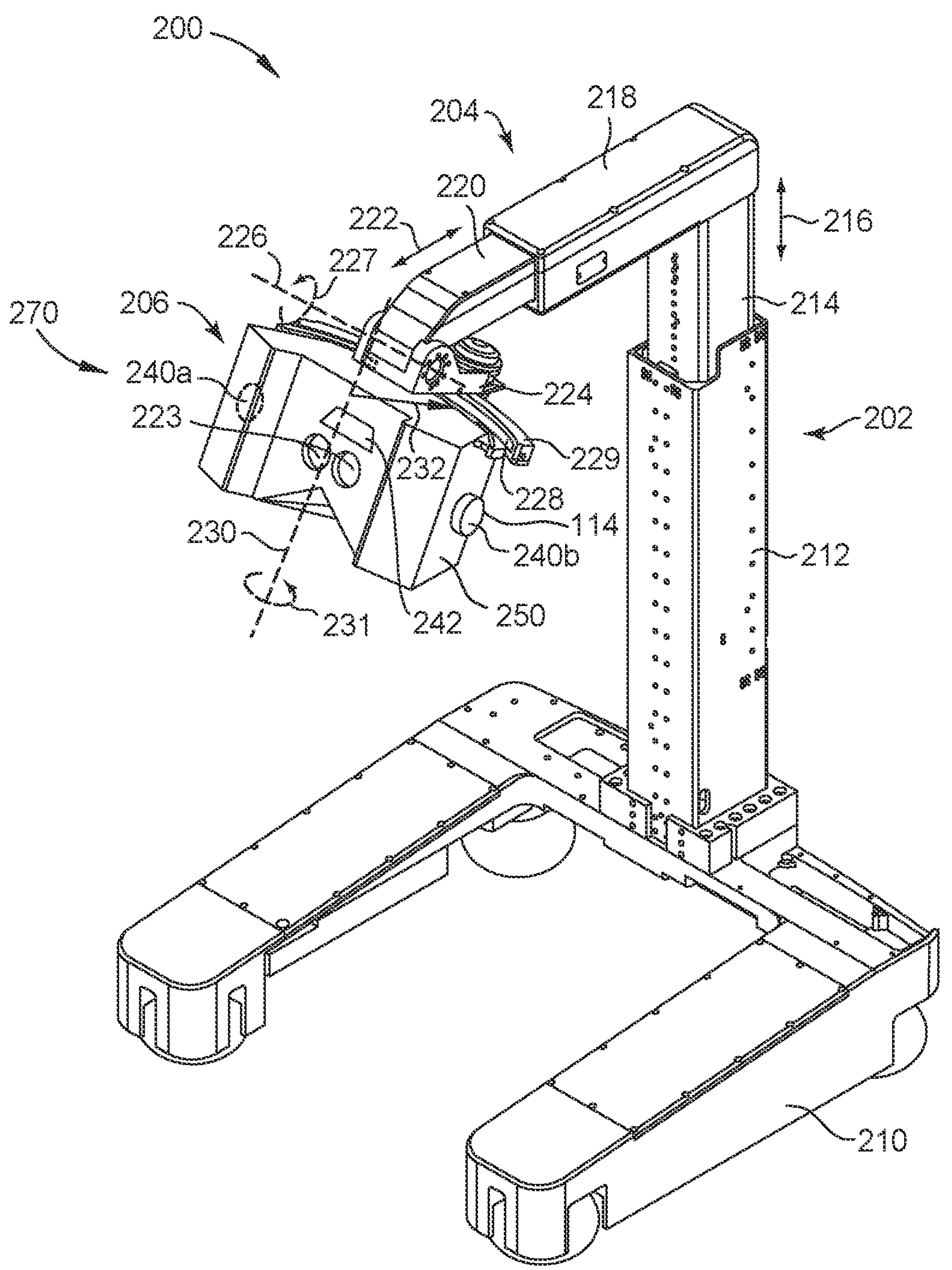
FIG. 2 is a perspective view of an example display system, according to various embodiments.

This description and the accompanying drawings that illustrate inventive aspects, embodiments, or modules should not be taken as limiting; the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

In this description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Further, the terminology in this description is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the elements or their operation in addition to the position and orientation shown in the figures. For example, if the content of one of the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes include various special element positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Elements described in detail with reference to one embodiment, or module may, whenever practical, be included in other embodiments, or modules in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, or application may be incorporated into other embodiments, or aspects unless specifically described otherwise, unless the one or more elements would make an embodiment or embodiments non-functional, or unless two or more of the elements provide conflicting functions.

In some instances, well known methods, procedures, components, and circuits have not been described in detail so as not to unnecessarily obscure aspects of the embodiments.

This disclosure describes various devices, elements, and portions of computer-assisted devices and elements in terms of their state in three-dimensional space. As used herein, the term "position" refers to the location of an element or a portion of an element in a three-dimensional space (e.g., three degrees of translational freedom along Cartesian x-, y-, and z-coordinates). As used herein, the term "orientation" refers to the rotational placement of an element or a portion of an element (three degrees of rotational freedom—e.g., roll, pitch, and yaw). As used herein, the term "shape" refers to a set positions or orientations measured along an element. As used herein, and for a device with repositionable arms, the term "proximal" refers to a direction toward the base of the computer-assisted device along its kinematic chain and "distal" refers to a direction away from the base along the kinematic chain.

Aspects of this disclosure are described in reference to computer-assisted systems and devices, which may include systems and devices that are teleoperated, remote-controlled, autonomous, semiautonomous, robotic, and/or the like. Further, aspects of this disclosure are described in terms of an embodiment using a medical system, such as the DA VINCI SURGICAL SYSTEM or ION SYSTEM commercialized by Intuitive Surgical, Inc. of Sunnyvale, California. Knowledgeable persons will understand, however, that inventive aspects disclosed herein may be embodied and implemented in various ways, including robotic and, if applicable, non-robotic embodiments. Embodiments described for DA VINCI SURGICAL SYSTEM are merely exemplary, and are not to be considered as limiting the scope of the inventive aspects disclosed herein. For example, techniques described with reference to surgical instruments and surgical methods may be used in other contexts. Thus, the instruments, systems, and methods described herein may be used for humans, animals, portions of human or animal anatomy, industrial systems, general robotic, or teleoperational systems. As further examples, the instruments, systems, and methods described herein may be used for non-medical purposes including industrial uses, general robotic uses, sensing or manipulating non-tissue work pieces, cosmetic improvements, imaging of human or animal anatomy, gathering data from human or animal anatomy, setting up or taking down systems, training medical or non-medical personnel, and/or the like. Additional example applications include use for procedures on tissue removed from human or animal anatomies (with or without return to a human or animal anatomy) and for procedures on human or animal cadavers. Further, these techniques can also be used for medical treatment or diagnosis procedures that include, or do not include, surgical aspects.

System Overview

FIG. 1 is a simplified diagram of an example computer-assisted device in the form of a teleoperated system 100, according to various embodiments. In some examples, the teleoperated system 100 may be a teleoperated medical system such as a telesurgical system. As shown, the teleoperated system 100 includes a follower device 104. The follower device 104 is controlled by one or more leader input devices 106, described in greater detail below. Systems that include a leader device and a follower device are also sometimes referred to as master-slave systems. Also shown in FIG. 1 is an input system that includes an operator input system 102 (e.g., a console or workstation), and in various embodiments the input system can be in any appropriate form and may or may not include an operator input system.

In this example, the operator input system 102 includes one or more leader input devices 106 which are contacted and manipulated by an operator 108 during use. For example, the operator input system 102 can comprise one or more leader input devices 106 for use by the hands of the operator 108. The leader input devices 106 in this example are supported by the operator input system 102 and can be mechanically grounded. An ergonomic support 110 (e.g., forearm rest) can be provided in some embodiments, on which the operator 108 can rest his or her forearms. In some examples, the operator 108 can perform tasks at a worksite near the follower device 104 during a procedure by commanding the follower device 104 using the leader input devices 106. The operator input system 102 may also include other operator input devices for controlling aspects of the teleoperated system 100, such hand actuated switches or buttons 107*a* and/or foot actuated pedals, buttons or switches 107*b*. The operator input system 102 may also include head actuated operator input devices for controlling aspects of the teleoperated system 100.

A display unit 112 is also included in the operator input system 102. The display unit 112 can display images for viewing by the operator 108. The display unit 112 can be moved in various degrees of freedom to accommodate the viewing position of the operator 108 and/or to optionally provide control functions as another leader input device. In one example, the display unit 112 includes hand controls 114 (which can, for example, be in the form of handles or knobs) that provide locations for the operator 108 to contact, grab, or grip and manually command the position and/or orientation of the display unit 112. In the example of the teleoperated system 100, displayed images can depict a worksite at which the operator 108 is performing various tasks by manipulating the leader input devices 106 and/or the display unit 112. In some examples, the images displayed by the display unit 112 can be received by the operator input system 102 from one or more imaging devices arranged at the worksite. In other examples, the images displayed by the display unit 112 can be generated by the display unit 112 (or by a different connected device or system), such as for virtual representations of tools, the worksite, or for user interface components.

When using the operator input system 102, the operator 108 can sit in a chair or other support in front of the operator input system 102, position his or her eyes in front of the display unit 112, manipulate the leader input devices 106, and rest his or her forearms on the ergonomic support 110 as desired. In some embodiments, the operator 108 can stand at the operator input system or assume other poses, and the display unit 112 and leader input devices 106 can be adjusted in position (height, depth, etc.) to accommodate the operator 108.

The teleoperated system 100 can also include the follower device 104, which can be commanded by the operator input system 102 while the teleoperated system 100 is in a teleoperation mode. In the teleoperation mode, operator inputs provided by the operator 108 to the leader input devices 106 are received by a control system 140 that is in communication with the operator input system 102 and the follower device 104. In the teleoperation mode, the control system 140 outputs commands to the follower device 104 based on the operator inputs provided to the leader input devices 106 such that the follower device 104 perform tasks at a worksite adjacent the follower device 104. In a medical example, the follower device 104 can be located near an operating table (e.g., a table, bed, or other support) on which a patient can be positioned. In such cases, the worksite can be provided on the operating table, e.g., on or in a patient, simulated patient, or model, etc. (not shown). The teleoperated follower device 104 shown includes a plurality of manipulator arms 120, each configured to couple to an instrument assembly 122. An instrument assembly 122 can include, for example, an instrument 126 and an instrument carriage configured to hold a respective instrument 126.

In various embodiments, one or more of the instruments 126 can include an imaging device for capturing images (e.g., comprising optical cameras, hyperspectral cameras, ultrasonic sensors, etc.). For example, one or more of the instruments 126 could be an endoscope assembly that includes an imaging device, which can provide captured images of a portion of the worksite to be displayed via the display unit 112.

In some embodiments, the follower manipulator arms 120 and/or instrument assemblies 122 can be controlled to move and articulate the instruments 126 in response to manipulation of leader input devices 106 by the operator 108, so that the operator 108 can perform tasks at the worksite. The manipulator arms 120 and instrument assemblies 122 are examples of repositionable structures on which instruments and/or imaging devices can be mounted. For a surgical example in the teleoperation mode, the operator 108 could direct the follower manipulator arms 120 using the input devices 106 to move instruments 126 to perform surgical procedures at internal surgical sites through minimally invasive apertures or natural orifices. Such instrument 126 may be configured to perform a task, such as but not limited to, obtaining an image, clamping, cutting, cauterizing, grasping, suturing, stapling, retracting, and suctioning, among other functions.

As shown, the control system 140 is provided external to the operator input system 102 and communicates with the operator input system 102. In other embodiments, the control system 140 may be provided in the operator input system 102 or in the follower device 104. As the operator 108 moves leader input device(s) 106, sensed spatial information including sensed position and/or orientation information is provided to the control system 140 based on the movement of the leader input devices 106. The control system 140 can determine or provide control signals to the follower device 104 to control the movement of the manipulator arms 120, instrument assemblies 122, and/or instruments 126 based on the received information and operator input. In one embodiment, the control system 140 supports one or more wired communication protocols, (e.g., Ethernet, USB, and/or the like) and/or one or more wireless communication protocols (e.g., Bluetooth, IrDA, HomeRF, IEEE 1002.11, DECT, Wireless Telemetry, and/or the like).

The control system 140 can be implemented on one or more computing systems. One or more computing systems can be used to control the follower device 104. In addition, one or more computing systems can be used to control components of the operator input system 102, such as movement of a display unit 112 and/or components thereof as further described below.

As shown, the control system 140 includes one or more processors 150 and a memory 160 storing a control module 170. In some embodiments, the control system 140 can include one or more processors, non-persistent storage (e.g., volatile memory, such as random access memory (RAM), cache memory), persistent storage (e.g., a hard disk, an optical drive such as a compact disk (CD) drive or digital versatile disk (DVD) drive, a flash memory, etc.), a communication interface (e.g., Bluetooth interface, infrared interface, network interface, optical interface, etc.), and numerous other elements and functionalities. In addition, functionality of the control module 170 can be implemented in any technically feasible software and/or hardware.

Each of the one or more processors 150 of the control system 140 can be an integrated circuit for processing instructions stored in the memory 160. For example, the one or more processors may be one or more cores or micro-cores of a processor, a central processing unit (CPU), a microprocessor, a field-programmable gate array (FPGA), an application-specific integrated circuit (ASIC), a digital signal processor (DSP), a graphics processing unit (GPU), a tensor processing unit (TPU), and/or the like. The control system 140 can also include one or more input devices, such as a touchscreen, keyboard, mouse, microphone, touchpad, electronic pen, or any other type of input device.

A communication interface of the control system 140 can include an integrated circuit for connecting the computing system to a network (not shown) (e.g., a local area network (LAN), a wide area network (WAN) such as the Internet, mobile network, or any other type of network) and/or to another device, such as another computing system.

Further, the control system 140 can include one or more output devices, such as a display device (e.g., a liquid crystal display (LCD), a plasma display, touchscreen, organic LED display (OLED), projector, or other display device), a printer, a speaker, external storage, or any other output device. One or more of the output devices may be the same or different from the input device(s). Many different types of computing systems exist, and the aforementioned input and output device(s) may take other forms.

In some embodiments, the control system 140 can be connected to or be a part of a network. The network can include multiple nodes. The control system 140 can be implemented on one node or on a group of nodes. By way of example, the control system 140 may be implemented on a node of a distributed system that is connected to other nodes. By way of another example, the control system 140 may be implemented on a distributed computing system having multiple nodes, where different functions and/or components of the control system 140 may be located on a different node within the distributed computing system. Further, one or more elements of the aforementioned control system 140 may be located at a remote location and connected to the other elements over a network.

Software instructions in the form of computer readable program code to perform embodiments of the disclosure can be stored, in whole or in part, temporarily or permanently, on a non-transitory computer readable medium such as a CD, DVD, storage device, a diskette, a tape, flash memory, physical memory, or any other computer readable storage medium. Specifically, the software instructions can correspond to computer readable program code that, when executed by a processor(s) (e.g., processor 150), is configured to perform some embodiments of the methods described herein.

In some embodiments, the one or more leader input devices 106 can be ungrounded instead of grounded as in the example above. Ungrounded leader input devices are not kinematically grounded, and include as an example leader input devices configured to be held by the hands of the operator 108 without additional physical support provided by the system. Such ungrounded leader input devices can be used in conjunction with the display unit 112. In some embodiments, the operator 108 can use a display unit 112 positioned near the worksite, such that the operator 108 manually operates instruments at the worksite, such as a laparoscopic instrument in a surgical example, while viewing images displayed by the display unit 112.

Some embodiments can include one or more components of a teleoperated medical system such as a DA VINCI SURGICAL SYSTEM or an ION SYSTEM, commercialized by Intuitive Surgical, Inc. of Sunnyvale, California, U.S.A. Embodiments described in reference to these systems are examples and should not to be considered as limiting the scope of the features disclosed herein. For example, different types of teleoperated systems having follower devices at worksites, as well as non-teleoperated systems, may make use of features described herein.

Figure 3:
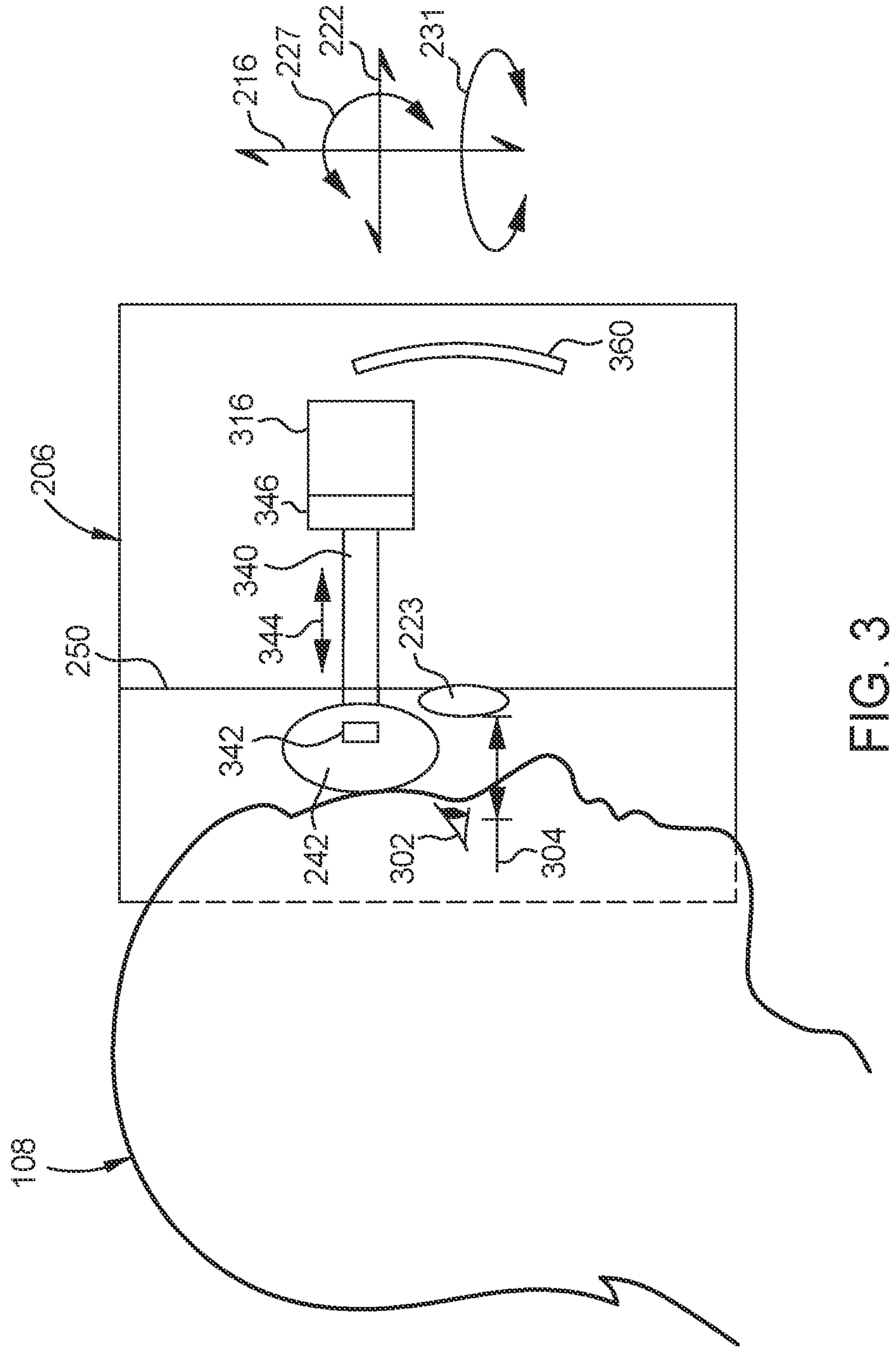
FIG. 3 is a schematic side view of an operator interfacing with a display unit of the example display system illustrated in FIG. 2, according to various embodiments.
Figure 4:
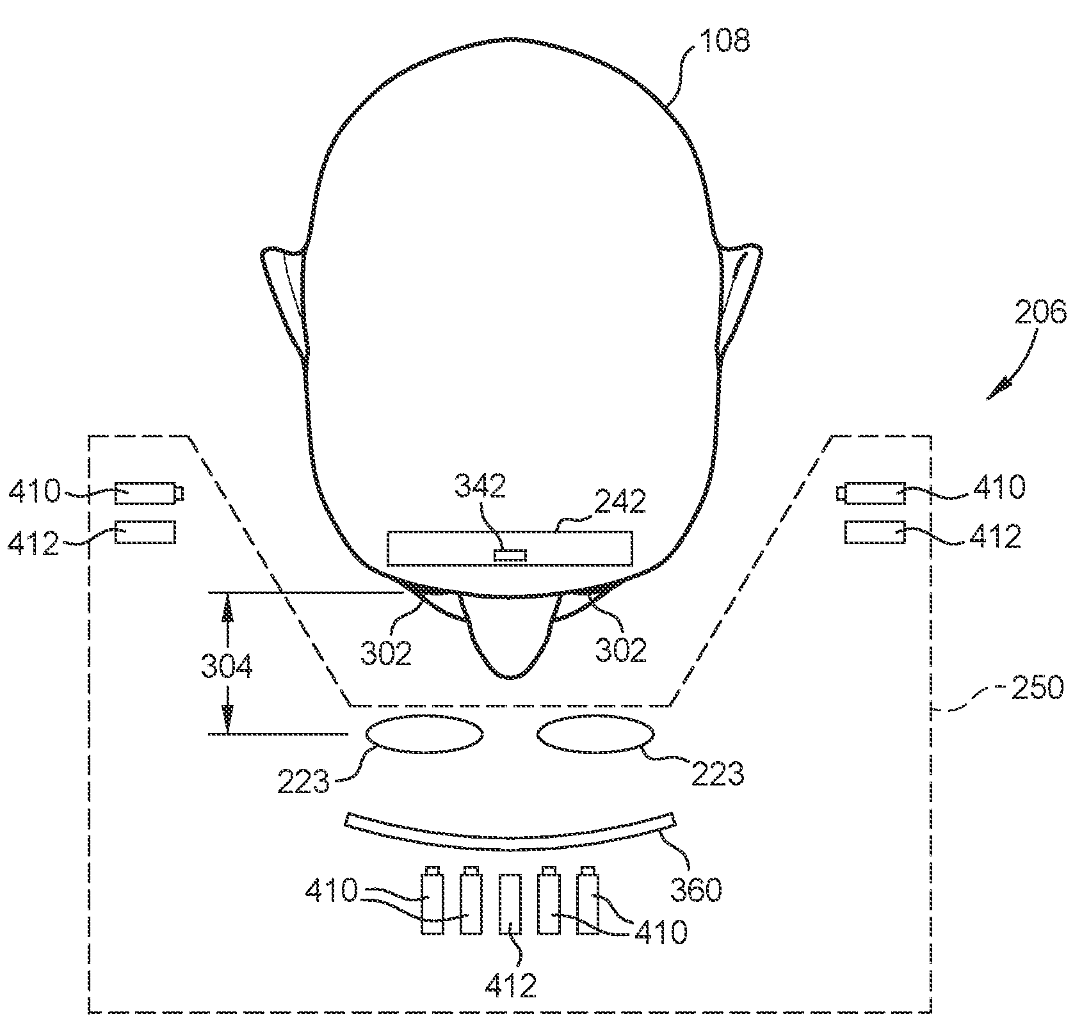
FIG. 4 is a schematic top view of an operator interfacing with a display unit of the example display system illustrated in FIG. 2, according to various embodiments.

FIG. 2 is a perspective view of an example display system 200, according to various embodiments. In some embodiments, the display system 200 is used in an operator input system of a teleoperated system (e.g., in the operator input system 102 of the teleoperated system 100 of FIG. 1), or the display system 200 can be used in other systems or as a standalone system, e.g., to allow an operator to view a worksite or other physical site, a displayed virtual environment, etc. Although FIGS. 2-4 show specific configurations of the display system 200, other embodiments may use display systems having different configurations.

As shown in FIG. 2, the display system 200 includes a base support 202, an arm support 204, and a display unit 206. The display unit 206 is provided with multiple degrees of freedom of movement provided by a support linkage including the base support 202, the arm support 204 coupled to the base support 202, and a tilt member 224 (described below) coupled to the arm support 204, where the display unit 206 is coupled to the tilt member 224.

The base support 202 may be a vertical member that is mechanically grounded, e.g., directly or indirectly coupled to ground, such as by resting on or being attached to a floor. For example, the base support 202 may be mechanically coupled to a wheeled support structure 210 that is coupled to the ground. The base support 202 includes a first base portion 212 and a second base portion 214 coupled such that the second base portion 214 is translatable with respect to the first base portion 212 in a linear degree of freedom (DOF) 216.

The arm support 204 may be a horizontal member that is mechanically coupled to the base support 202. The arm support 204 includes a first arm portion 218 and a second arm portion 220. The second arm portion 220 is coupled to the first arm portion 218 such that the second arm portion 220 is linearly translatable in a first linear degree of freedom (DOF) 222 with respect to the first arm portion 218.

The display unit 206 includes a housing 250 that is mechanically coupled to the arm support 204. The housing 250 and display unit 206 may be moveable in other linear DOFs provided by the linear translations of the second base portion 214 and the second arm portion 220.

In some embodiments, the housing 250 of the display unit 206 includes a display device 360, e.g., one or more display screens, projectors, or other display devices, that may display digitized images. In the example shown, the display unit 206 further includes lenses 223 that provide viewports in the housing 250 through which the display device 360 can be viewed. Any technically feasible lenses can be used in embodiments, such as lenses having high optical power. Although display units that include lenses, through which images are viewed, are described herein as a reference example, some embodiments of display units may not include such lenses. For example, in some embodiments, the images displayed by a display unit can be viewed via an opening that allows the viewing of displayed images, viewed directly as displayed by a display device 360 of the display unit 206, or in any other technically feasible manner.

In some embodiments, the display device 360 of the display unit 206 displays images of a worksite (e.g., an interior anatomy of a patient in a medical example), captured by an imaging device such as an endoscope. The images may alternatively depict a virtual representation of a worksite. The images may show captured images or virtual renderings of instruments 126 of the follower device 104 while one or more of these instruments 126 are controlled by the operator via the leader input devices (e.g., the leader input devices 106 and/or the display unit 206) of the operator input system 102.

In some embodiments, the housing 250 of the display unit 206 is rotationally coupled to the arm support 204 by a tilt member 224. In the illustrated example, the tilt member 224 is coupled at a first end to the second arm portion 220 of the arm support 204 by a rotary coupling configured to provide rotational motion of the tilt member 224 and the display unit 206 about the tilt axis 226 with respect to the second arm portion 220.

Each of the various degrees of freedom discussed herein may be passive and require manual manipulation for movement, or be movable by one or more actuators, such as by one or more motors, solenoids, etc. For example, the rotational motion of the tilt member 224 and the display unit 206 about the tilt axis 226 can be driven by one or more actuators, such as by a motor coupled to the tilt member at or near the tilt axis 226.

The housing 250 of the display unit 206 can be rotationally coupled to the tilt member 224 and can rotate about a yaw axis 230. For example, rotation about the yaw axis 230 can be a lateral or left-right rotation from the point of view of an operator viewing images displayed by the display unit 206. In this example, the display unit 206 is coupled to the tilt member 224 by a rotary mechanism which can comprise a track mechanism that constrains the motion of the display unit 206. For example, in some embodiments, the track mechanism includes a curved member 228 that slidably engages a curved track 229, thus allowing the display unit 206 to rotate about the yaw axis 230 by moving the curved member 228 along the track 229. The location of the yaw axis 230 is generally at the origin of a radius 232 defined by the curvature of the track 229. As shown, rotation of the display unit 206 provides a DOF 231 in a lateral or left-right rotation about the yaw axis 230 from the point of view of the operator viewing images displayed by the display unit 206.

The display system 200 can thus provide the display unit 206 with a first translational DOF 216 (a vertical, linear DOF in this example), a second translational DOF 222 (a horizontal, linear DOF in this example), a first rotational DOF 227 (a tilt-enabling DOF in this example) and a second rotational DOF 231 (a yaw-enabling DOF in this example). A combination of coordinated movement of components of the display system 200 in these degrees of freedom allow the display unit 206 to be positioned at various positions and orientations based on the preferences of an operator. The enabled motion of the display unit 206 in the various freedom allows a headrest 242 coupled to the housing 250 to move relative to a head of the operator 108, or to keep in place relative to the head as the operator 108 moves within a world frame. For example, the motion of the display unit 206 stay close to, or maintain contact with, the head of the operator 108, such as when the operator 108 is providing head input through head motion when the display system 200 is in a steerable viewer mode. In the steerable viewer mode, the operator 108 can move his or her head to provide input to control the display unit 206 to follow the motion of the head, and motions of the head can further optionally control the position and/or orientation of one or more imaging devices that capture images displayed via the display unit 206. Although some embodiments are described herein as including a steerable viewer mode, other embodiments may not include a steerable viewer mode. In embodiments with and without steerable viewer modes, the position and/or orientation of one or more imaging devices that capture images displayed via the display unit 206 may be controlled using devices other than display unit 206, such as via the leader input devices 106 that are manipulated by the hands of an operator.

Any repositionable device that supports the display unit 206 and provides the display unit 206 with degrees of freedom and ranges of motion appropriate for the application may be used in lieu of the configuration shown in FIG. 2. Additional examples of moveable display systems are described in U.S. Provisional Patent Application No. 62/890,844, filed Aug. 23, 2019, and entitled "Moveable Display System," and International Patent Application No. PCT/US2020/047494, filed Aug. 21, 2020, and entitled "Moveable Display System," both of which are incorporated by reference herein.

It is understood that FIG. 2 merely shows an example for a configuration of a display system. Alternative configurations supporting movement of the display unit 206 based on an input from the operator are also possible. For example, the housing 250 includes one or more grab hand controls 114 that provide an interface for the operator 108 to grab the housing 250 and reposition the display unit 206. The hand controls 114 may also include sensors (e.g., motion sensors, switches, etc.) 240*a*, 240*b* that provide signals to control system 140. Control system 140 can process these or other signals to command any motion control devices to control the pose of the display unit 206, to allow the housing 250 to be moved manually, to move the display unit 206 using motorized or pneumatic actuators, or to command actuators or brakes to allow the display unit 206 to be moved. Optionally, the sensors 240*a*, 240*b* also provide signals indicate of the magnitude and/or direction of forces or torques applied to the hand controls 114, to the housing 250, such as by the operator 108. The control system 140 can process such signals for allowing or commanding movement of the display unit 206 in one or more directions and/or orientations.

Although the display unit 206 is described herein primarily as part of a grounded mechanical structure (e.g., the display system 200), in other embodiments, the display unit 206 may be ungrounded, such as head-mounted or user-supported augmented-reality or virtual-reality systems. Further, display unit 206 may include any technically feasible display device 360 or other devices. In all of these cases, the position and/or orientation of the display unit 206 may be determined using one or more sensors (e.g., parts of a sensor system 270) of the display system 200. The sensor system 270 may include one or more accelerometers, gyroscopes, inertial measurement units, image capturing devices such as cameras or other imagers, distance sensors, proximity sensors, and/or other sensors located internally or externally to the display unit 206. The sensors 240*a*, 240*b* described above are part of the sensor system 270. Some of the sensors of the sensor system 270, as further described below, are coupled to the control system 140 and utilized to detect input provided by the operator 108, or to detect the interaction, position, and/or orientation of the operator 108 relative to display unit 206 or one or more components of the display unit 206. Some of the sensors of the sensor system 270 may also be, or may alternatively be, utilized to detect the interaction, position, and/or orientation of one or more components of the display unit 206 relative to other components, such as relative to other components of the display unit 206 or of some other equipment, persons, or the surrounding environment.

As discussed above, the headrest 242 is coupled to the display unit 206. The headrest 242 is positioned on a part of the display unit 206 that is facing the forehead of the operator 108 when the operator 108 is viewing images shown by the display unit 206. The headrest 242 is configured to be able to contact the forehead of the operator 108. The headrest 242 provides a location indicator a contact surface for the operator 108, to aid the operator 108 in more comfortably viewing images shown by the display unit 206 and operate the teleoperated system 100 more effectively, such as with improved precision, greater comfort, faster speed, less frustration, and/or less fatigue. The headrest 242, is movable relative to one or both of the operator 108 and the display unit 206. The headrest 242 is movable relative to the operator 108 and/or the display unit 206 while the teleoperated system 100 is in a headrest adjustment mode. In the headrest adjustment mode, motion of the headrest 242 is enabled by the control system 140 as further discussed below. To reduce undesired motion of the headrest 242 while the follower device 104 of the teleoperated system 100 is actively being commanded while in the teleoperation mode, the control system 140 is configured to enforce a temporal non-overlap of (i) teleoperation of the follower device 104 based on operator input received at the input device 106, and (ii) physical adjustment to the headrest. Stated differently, the control system 140 prevents the teleoperated system 100 from allowing both the teleoperation of the follower device 104 and the physical adjustment of the headrest at the same time, even if both the teleoperated and headrest adjustment modes are requested by the operator. As a result, inadvertent motion of the headrest during operation of the teleoperated system 100 during teleoperation of the follower device 104 is substantially prevented. This helps to mitigate inadvertent head movement that potentially could impact the operation of the teleoperated system 100. In another example, the control system 140 may be configured to enforce a temporal non-overlap of the teleoperation mode and the headrest adjustment mode. Stated differently, the control system 140 prevents the teleoperated system 100 from being in both the teleoperation mode and the headrest adjustment mode at the same time.

FIG. 3 is an enlarged schematic detail of an operator 108 interfacing with the display unit 206. FIG. 3 illustrates some of the mechanisms and associated sensors of the sensor system 270 utilized to control the position of the headrest 242.

The sensor system 270 may include one or more distance sensors 422 mounted to the housing 250 on the side of the lenses 223. In such an embodiment, the distance sensors 422 located to either side of the head of the operator 108. The distance sensors 422 may also or alternatively be configured and/or positioned not only to derive the location of the eyes 302 of the operator 108, but also the location and/or orientation of the head of the operator 108 relative to the housing 250 of the display unit 206. Examples of suitable distance sensors 422 include ultrasonic distance sensors, infrared (IR) distance sensors, laser distance sensors (LIDAR), and time-of-flight sensors, among others.

In another example, the sensor system 270 includes one or more sensors 410, such as a camera or other imaging device, that may be utilized to determine the distance 304 between the eyes 302 of the operator 108 and the housing 250 or other portion of the display unit 206. The one or more sensors 410 may additionally or alternatively be utilized to determine the distance or orientation of the head of the operator 108 to the housing 250 or other portion of the display unit 206. The one or more sensors 410 may be used additionally with, or in the alternative to, the distance sensors 412.

In some examples, a sensor 410 such as a camera can be placed behind each lens 223, or elsewhere, to captures images of one or both eyes 302 of the operator 108. In the addition or in the alternative, the sensor 410 may be utilized to provide a metric indicative of the distance of the operators head from a portion of the display unit 206, which can be utilized to determine the position of the operators head relative to the display unit 206. In FIG. 4, sensors 410 are placed behind each of the lenses 223 and the display device 360. The display device 360 may be configured as a half-silvered mirror which can conceal the sensors 410 from the operator 108, according to various embodiments. In some examples, a pair of cameras or other sensors 410 can be placed behind each lens 223, or elsewhere, to capture stereo images of one or both eyes 302 of the operator 108. The stereo images of one or both eyes 302 captured by the sensors 410 may be utilized to determine if the position of the eye 302 is in a target location, for example in a position that provides better focus and/or fusing of displayed images. Display images can be projected onto or otherwise visible by the display device 360 in some embodiments. In one example, the sensors 410 may be utilized to detect that the gaze of the operator 108 is directed toward the display device 360. In another example, the sensors 410 may be utilized to determine that a position of the operator 108 or of the operator's eyes 302, relative to a position or orientation of the display unit 206 or display device 360, is outside a target physical relationship. In yet another example, the sensors 410 may be utilized to determine that an optical relationship between the eye 302 of the operator 108 and an image displayed by the display device 360 of the display unit 206 is outside a target optical relationship. The target optical and physical relationships may be stored in the memory 160 of the control system 140, be a manually selected, determined by the control system 140 through machine learning techniques, or selected or retrieved by the control system 140 via another technique.

Cameras or other imaging devices of the sensor system 270 for determining the eyes or head location can be placed elsewhere in other embodiments. For example, side sensors 420, such as cameras, of the sensor system 270 may be placed on the lateral sides of the housing 250. Thus, when the operator 108 engages the display unit 206, the side sensors 420 can determine the position of the eyes and/or head of the operator, which can be utilized to determine the relative position and/or orientation of the operator's head and/or eyes relative to the lenses and/or other portion of the display unit 206. In one example, the side sensors 420 may be utilized to detect that the gaze of the operator 108 is directed toward the display device 360.

Alternatively to, or in addition to, the side sensors 420 described above, other distance sensors 422 of the sensor system 270 may be coupled to the lateral sides of the housing 250. Thus, when the operator 108 engages the display unit 206, the distance sensors 422 can determine the position of the eyes and/or head of the operator, which can be utilized to determine the relative position and/or orientation of the operators head and/or eyes relative to the lenses and/or other portion of the display unit 206.

In some examples as further described below, the headrest 242 can be moved in the inward-outward direction relative to the display unit 206 so that the head of the operator 108, that is in contact with the headrest 242, is moved closer or farther away relative to the lenses 223, or other portion(s) of the display system 200. Then, the control system 140 can issue commands to a controller for one or more joints of a repositionable structure to which the headrest 242 is mounted to cause movement of the headrest 242 according to the determined movement. For example, based on the determined movement, the control system 140 can issue one or more commands, directly or indirectly, to an actuator 316 as described below to move the headrest 242 such that the eyes 302 of the operator 108 are moved to the target distance relative to the lenses 223, or according to another target parameter. It should be noted that the head of the operator 108 should remain in contact with the headrest 242 when the headrest 242 is moved in order for the eyes 302 and/or other portion(s) of the head of the operator 108 to be moved relative to the lenses 223 or the other portion(s) of the display system 200, unlike the examples of moving the display unit 206 described above, which do not require the head of the operator 108 to be in contact with the headrest 242. Although described herein primarily with respect to moving the headrest 242 in the inward-outward direction, in other embodiments the headrest 242 may also be moved in other directions and/or rotations, such as about the yaw axis 230 based on a motion of the eyes 302 of the operator 108.

The distance 304 between eyes 302 of the operator 108 and the lenses 223 may be selected to enhance the image quality provided to the operator 108. The distance 304 can be derived from information obtained from the sensor system 270. The position of the lenses 223 may be set at a target parameter, such as a target distance or a target location, relative to the eyes 302 of the operator 108, or other portion(s) of the head of the operator 108. For example, the target parameter could be a distance from the lenses 223 to a focal point (not shown) associated with the lenses 223 or a distance from the lenses 223 to a viewing zone (not shown) within which eyes 302 of the operator 108 can perceive acceptable viewing of information displayed by the display unit 206 through the lenses 223. Repositioning portion(s) of the display system 200 such as the headrest 242 according to the target parameter can improve the operators view of images being displayed by display unit 206, such as an increase in the ability of the operator 108 to see an entire image being displayed via the display unit 206 and/or see a properly fused image that combines images seen by different eyes. The target parameter may be defined in part based on the type of lenses included in a display unit, the type of display unit, a calibration procedure, and/or operator preference, among other things. For example, the target parameter can be a 15-20 mm separation distance in some embodiments. In some embodiments, the target parameter can be set to a distance of the eyes 302 (or other portion(s) of the head of the operator 108) from portion(s) of the display system 200, such as the lenses 223, or a location of the portion(s) of the display system 200 relative to the eyes 302, at the completion of a manual adjustment to the position of the display unit 206 by the operator 108. For example, the operator 108 could engage one of the input devices 106, 107*a*, 107*b* or other input device to cause the display unit 206, and/or headrest 242 to be moved so that the operator 108 can view displayed images comfortable. These operator 108 adjustments can be part of a calibration procedure, and the target parameter can be set to the distance from the eyes 302 (or other portion(s) of the head of the operator 108) to the portion(s) of the display system 200, or the location of the portion(s) of the display system relative to the eyes 302 (or other portion(s) of the head of the operator 108) at the completion of the adjustments.

Returning to FIG. 3 and as briefly discussed above, the headrest 242 is movable relative to the display unit 206. The headrest 242 may include and/or be engaged with the sensor system 270 so that positional information, force, torque or other information relating to the engagement between the operator 108 and the headrest 242, and/or the engagement between the headrest 242 and the display unit 206 may be derived. In the example depicted in FIG. 3, the headrest 242 includes a head-input sensor 342 of the sensor system 270. The head-input sensor 342 senses inputs applied to the headrest 242 by the operator 108. The head-input sensor 342 can include any of a variety of types of sensors, e.g., resistance sensors, proximity sensors, capacitive sensors, force sensors, optical sensors, etc. In some embodiments, the head-input sensor 342 is configured to sense contact of the headrest 242 with the forehead of the operator 108 while the operator is viewing images displayed by the display unit 206. In some embodiments, the head-input sensor 342 is configured to support non-contact input, by sensing the position, orientation, motion (velocity direction and/or magnitude, acceleration direction and/or magnitude) when the forehead of the operator 108 is proximate to the headrest 242.

The headrest 242 is coupled to a repositionable structure 340 disposed in the housing 250 of the display unit 206. The repositionable structure 340 allows motion of the headrest 242 relative to the housing 250 in at least one spatial degree of freedom (DOF). For example, the repositionable structure 340 may allow the headrest 242 to move in a multiple degrees of freedom. In another example, the repositionable structure 340 may constrain the headrest 242 to move in a single spatial degree of freedom. In the example depicted in FIG. 3, the motion of the headrest 242 is constrained by the repositionable structure 340 to move in a DOF 344 that is linear. The linear DOF 344 may be a translation towards or away from a portion of the housing 250 of the display unit 206 that faces the front of the operator 108. The repositionable structure 340 may be a linkage, a linear slide, ball screw, linear actuator, or other suitable structure which allows the headrest 242 to be moved relative to the housing 250 of the display unit 206 by manual manipulation and/or by one or more actuators 316.

The one or more actuators 316 operable to control the motion of the headrest 242 through the repositionable structure 340 may be an electric or air motor, mechanical, hydraulic, pneumatic, or piezoelectric actuator, or other suitable motion control device. In examples in which the repositionable structure 340 move through a single DOF, such as the DOF 344 illustrated in FIG. 3, a single actuator 316 may be utilized to move the headrest 242. In other examples in which the repositionable structure 340 move through two or more DOFs, a plurality of actuators 316 may be utilized to move the headrest 242. The actuator 316 may include a sensor 346 which is part of the sensor system 270. The sensor 346, such as an encoder, provides information that allows the position of the headrest 242 relative to the housing 250 to be determined. In other examples, the sensor 346 may be included in the headrest 242 and/or the repositionable structure 340 rather than the actuator 316. In some examples, the sensor 346 may be utilized to provide sensor data indicative of the force and/or torque applied to the headrest 242 by the operator 108.

The position of the headrest 242 may be controlled manually or through the use of the control system 140. In one example, headrest 242 is externally manipulable, such as by the hands of the operator. In another example, the actuator 316 is commanded by the control system 140 to move the headrest 242 though an input provided by the operator 108 using one of the input devices 106, 107*a*, 107*b* or one or more hand controls 114. For example, one of the input devices may be a three position switch having a first position that signals to the control system 140 to command the actuator 316 to extend the headrest 242 away from the housing 250 of the display unit 112 and towards the operator 108, a second position that signals to the control system 140 to command commands the actuator 316 to retract the headrest 242 towards the housing 250 of the display unit 112 and away from the operator 108, and a third position that causes the actuator 316 not to move the headrest 242.

In another example, the control system 140 provides commands to the actuator 316 to move the headrest 242. The actuator control commands may be based on input obtained from one or more of the sensors of the sensor system 270 that provides an indication that the headrest 242 should be moved. The input from the various sensors utilized to command motion of the headrest 242 is described further below. The actuator control commands may be alternatively selected by the operator 108 from a digital menu displayed on the display device 360. The operator 108 may select motion commands from the digital menu utilizing one of the input devices or other suitable technique.

In one example, the control system 140 commands the headrest actuator 316 to maintain a position of the headrest 242 in a common frame while the control system 140 moves the display unit 206 relative to the common frame. For example, the control system 140 can coordinate motion control signals to the headrest actuator 316 and to actuators (not shown) that control the motion of the display unit 206 in any one or combination of the DOF's 216, 222, 227, 231, 344 so that the headrest 242 is maintained stationary in the common frame as the display unit 206 moves.

In another example, the control system 140 commands headrest actuator 316 to change a position of the headrest 242 in a common frame of reference while the control system 140 maintains a position of the display unit 206 in the common frame. For example, the control system 140 can coordinate motion control signals to the headrest actuator 316 and to actuators (not shown) that control the motion of the display unit 206 in any one or combination of the DOF's 216, 222, 227, 231, 344 so that the display unit 206 is maintained stationary in the common frame as the headrest 242 moves relative to the display unit 206.

In another example, the control system 140 commands both the headrest actuator 316 to change a position of the headrest 242 and the actuators (not shown) that control the motion of the display unit 206 in any one or combination of the DOF's 216, 222, 227, 231, 344 so that the display unit 206 and the headrest 242 moves in the common frame. The display unit 206 and the headrest 242, although both moving in the common frame, may or may not move relative to each other.

In another example, the control system 140 provides commands headrest actuator 316 to move the headrest 242 relative to the display unit 206 in a direction corresponding to a direction of a force and/or torque applied to the headrest 242. For example, the control system 140 can provide motion control signals to the headrest actuator 316 so that the headrest 242 moves relative to the display unit 206 independent of movement (or lack of movement) of the display unit 206. The force and/or torque applied to the headrest 242 by be sensed by one or more of the sensors 342, 346, or another sensor of the sensor system 270 included with the display unit 206.

In another example, the control system 140 provides commands headrest actuator 316 to move the headrest 242 relative to the display unit 206 based on information sensed by the sensor system 270 of the display unit 206. Some of the sensors of the sensor system 270 that may provide information utilized to comment the headrest to move include but is not limited to the sensors 342, 346, 410, 412, 420 and 422. Information provided by one or more of these sensors can provide an indication that headrest adjustment mode should be entered, and/or that the headrest should be repositioned. For example, one or more of the sensors 342, 346, 410, 412, 420 or 422 may be configured to detect a motion of a head of the operator 108. In response to the detection of the head motion, the control system 140 may command the headrest actuator 316 to move the headrest 242. The command to move the headrest 242 may include a directionality of the motion and a distance to move the headrest 242. The command to move the headrest 242 may alternatively include a target position to which the headrest 242 it to be moved.

In another example, one or more of the sensors of the sensor system 270 may be configured to detect a force applied to the display unit 206. In response to the detection of the force and/or torque applied to the display unit 206, the control system 140 may command the headrest actuator 316 to move the headrest 242. The command to move the headrest 242 may include a directionality of the motion and a distance to move the headrest 242 that is based on a directionally of the force and/or torque applied to the display unit 206. The force and/or torque applied to the display unit 206 may be provided by the sensors 240*a*, 240*b* engaged with the hand controls 114. Alternatively, force and/or torque applied to the display unit 206 may be provided by the sensors 342 and 346 included in the display system 200.

In another example, the sensor system 270 may be configured to detect a force applied to the headrest 242. In response to the detection of the force and/or torque applied to the headrest 242, the control system 140 may command the headrest actuator 316 to move the headrest 242. The command to move the headrest 242 may include a directionality of the motion and a distance to move the headrest 242 that is based on a directionally of the force and/or torque applied to the headrest 242. The force and/or torque applied to the headrest 242 may be provided by the sensors 342, 346 included in one or more of the headrest 242, repositionable structure 340 and/or headrest actuator 316. Alternatively, force and/or torque applied to the headrest 242 and/or display unit 206 may be provided by other sensors of the sensor system 270 interfaced with the display system 200.

In another example, the force and/or torque applied to the headrest 242 detected by the sensor system 270 may be utilized by the control system 140 to command the headrest actuator 316 (and/or actuators controlling the DOF's of the operator input system 102) to move the headrest 242 in a manner that follows the motion of the head of the operator 108. For example, the control system 140 may command the headrest actuator 316 to move the headrest 242 to follow the motion of the head of the operator 108 such that the head of the operator 108 remains in contact with the headrest 242. Alternatively in some instances where the sensor system 270 supports non-contact sensing of the head of the operator 108, and based on operator 108 preference, the control system 140 may command the headrest actuator 316 to move the headrest 242 to remain at a defined distance relative to the head of the operator 108).

In another example, the control system 140 may command the headrest actuator 316 to move the headrest 242 to follow the motion of the head of the operator 108 such that the head of the operator 108 remains in contact (or in proximate non-contact in the example instances described in the paragraph above) with the headrest 242 utilizing the information provided the sensors 342, 346 interfaced with one or more of the headrest 242, repositionable structure 340 and/or headrest actuator 316, and/or other sensor of the sensor system 270. The force generated by the actuator 316 urges the headrest 242 against the forehead of the operator 108 so as the operator moves, the headrest 242 follows the motion of the operator's head. The force generated by the actuator 316 may be modeled as virtual spring/damper. The force may increase towards a desired constant force over time, such as when the motion of the operators head slows or becomes motionless. In one example, the force provided by the actuator 316 to the headrest 242 is ramped to a constant force as the headrest 242 moves from an initial position to a final position at or near the position that the operators head approaches zero velocity, moves in increasingly small increments, or when acceleration of the head decreases.

In another example, the sensor system 270 may be configured to detect one or more metrics associated with the eyes 302 of the operator 108, and in response to this detection, the control system 140 may command the headrest actuator 316 to move the headrest 242 to move or not based on the detected metric. For example, information provided by at least one of the sensors 410, 412, 420, 422 can provide a metric indicative of the distance 304 between the eyes 302 of the operator 108 and the lenses 223 (or other portion of the display unit 112. The metric may be utilized by the control system 140 to command the headrest actuator 316 to move the headrest 242 to maintain the distance 304 at a predetermined value, such as a target distance. The predetermined value of the distance 304 may be stored in memory 160 of the control system 140. The predetermined value of the distance 304 may be selected by the operator 108, be in a look-up table, be a preset parameter, or be learned by the control system 140 through use of the operator input system 102 through machine learning techniques. In one example, the metric indicative of a distance may be detected by the sensors 410, 420 by sensing a directional gaze of the operator 108 towards the lenses 223. In another example, the metric indicative of a distance may be detected by the sensors 410, 412, 420, 422 by sensing a distance of the operator 108 from the lenses 223. In yet another example, the metric associated with the eyes 302 of the operator 108 may be detected by the sensors 410, 412, 420, 422 by a positional relationship or an orientation of the head or eyes 302 operator 108 relative to a portion of the display unit 206, such as one or more of the lenses 223, the housing 250, or the display device 360 of the display unit 206. The sensed positional or orientation relationship may be compared to a target distance or orientation relationship, and if the sensed positional or orientation relationship is outside of the target positional or orientation relationship, the control system 140 commands the headrest actuator 316 to move the headrest 242 to a position that the sensed positional/orientation relationship is equal to the target distance/orientation relationship. In one example, the headrest actuator 316 moves the headrest 242 until the sensed positional and/or orientation relationship satisfies the target positional and/or orientation relationship. The target positional or orientation relationship may be selected by the operator 108, be in a look-up table, be a preset parameter, or be learned by the control system 140 through use of the operator input system 102 through machine learning techniques.

The information provided by the sensors detecting the force and/or torque applied to the headrest 242 may be processed by the control system 140 to discern if the force and/or torque applied to the display unit 206 is likely applied by a specific body part of the operator 108, such as a forehead or hand. For example, the directionality of force and/or magnitude of the force and/or torque applied to the headrest 242 may be indicative that the force and/or torque was applied to the headrest 242 by a hand of the operator rather than the operator's head. Conversely, the directionality of force and/or magnitude of the force and/or torque applied to the headrest 242 may be indicative that the force and/or torque was applied to the headrest 242 by the head of the operator 108 rather than another part of the operator. Stated differently, the control system 140 utilizing information provided by the sensors is able to determine that the operator interactions with the headrest 242 is performed with the body part other than the head by determining that a temporal history of force and/or torque applied to the headrest 242 is inconsistent with head interaction, or determining that the temporal history of the force and/or the torque applied to the headrest 242 is consistent with hand interaction. The temporal history of force and/or torque applied to the headrest 242 may be generated over time utilizing information provided by the sensors and stored in the memory 160 of the control system 140, or be provided as a predefined criteria that is retrieval from the memory 160 or other storage device by the control system 140. In one example, the temporal history of a force and/or torque applied to the headrest 242 may be selected from the group consisting of pulling then pushing on the headrest, tapping on the headrest, wiggling the headrest, twisting the headrest, and pushing on the headrest for longer than a predetermined duration of time.

In some examples, information provided by the sensors may be utilized to determine if an adjustment mode criteria set is satisfied prior to commanding the headrest actuator 316 and/or switching between teleoperation and headrest adjustment modes. The adjustment mode criteria set may be stored in the memory 160 or otherwise available to the control system 140. In some examples, the adjustment mode criteria set may be a predefined condition of the control system 140, or derived from information obtained from one or more of the sensors interfaced with the display system 200. The adjustment mode criteria set may be a setting, state or mode of the teleoperated system 100. For example, the adjustment mode criteria set may be (i) a determination, for example made using information provided by the sensors or the control system 140, that the sensor information meets criteria stored in the memory 160 of the control system 140; (ii) that the operator 108 is engaged with the operator input system 102; (iii) that a hand of the operator 108 is engaged with the display unit 206; (iv) that a head of the operator 108 is engaged with the display unit 206; (v) that a gaze of the operator 108 is directed toward an image displayed by the display unit 206; (vi) that the control system 140 is in a manual adjustment mode; and/or (vii) that the control system 140 is in a headrest adjustment mode. The adjustment mode criteria set is compared against information obtained from one or more of the sensors interfaced with the display system 200, or a setting, state or mode of the teleoperated system 100, and if the adjustment mode criteria set is satisfied, the control system 140 either commands the headrest actuator 316 to move and/or switches between teleoperation and headrest adjustment modes.

In some examples, information provided by the sensors of sensor system 270 may be utilized to determine an inward-outward movement of the display unit 206 in one or more of the degrees of freedom 216, 222, 227, 231, 344 relative to the headrest 242 and/or lenses 223. For example, the control system 140 can further command the actuator 316 in the repositionable structure 340, or in another repositionable structure, to move the headrest 242 relative to the display unit 206 by a same magnitude and in an opposite direction (also referred to herein as a "complementary motion") so that a position of the headrest 242 and a head position of the operator 108 are not changed. In such cases, the headrest 242 can remain substantially stationary while other joints of the repositionable structure are moved to move the display unit 206. For example, in some embodiments, the display system 200 includes a repositionable structure having a number of degrees of freedom that can be used to move the display unit 206 and an additional degree of freedom that can be used to move the headrest 242. An example complementary motion of the headrest 242 by a same magnitude and in an opposite direction to the movement of the display unit 206, for example to cause the headrest 242 to move closer to the display unit 206 when the motion of the display unit 206 is moved toward the operator 108. The control system 140 can issue one or more commands, directly or indirectly, to one or more actuators (e.g., actuator 316) that cause the headrest 242 to move according to the complementary movement. In particular, in some embodiments, the control system 140 and/or operator-manipulated input devices (e.g., 106, 107*a*, 107*b*, 114) can communicate, directly or indirectly, with the sensor 346 interfaced with the actuator 316 to cause the desired motion of the headrest 242 in at least one or more DOFs.

In some embodiments in which the headrest 242 is repositioned, the control system 140 repositions portion(s) of the display unit 206 independent of the motion of the headrest 242. For example, the headrest 242 may be repositioned according to a first target parameter, while a portion of the display unit 206 is repositioned according to a second target parameter when the teleoperated system 100 is in the headrest adjustment mode. As described above, the teleoperated system 100 does not permit physical adjustment of the headrest during teleoperation of the follower device 104 in response to operator input received at an operator input device 106. Methods for operating the teleoperated system 100 in a manner that the control system 140 enforces the temporal non-overlap of the teleoperation of the follower device 104 and physical adjustment of the headrest are further discussed below.

System Operation

Figure 5:
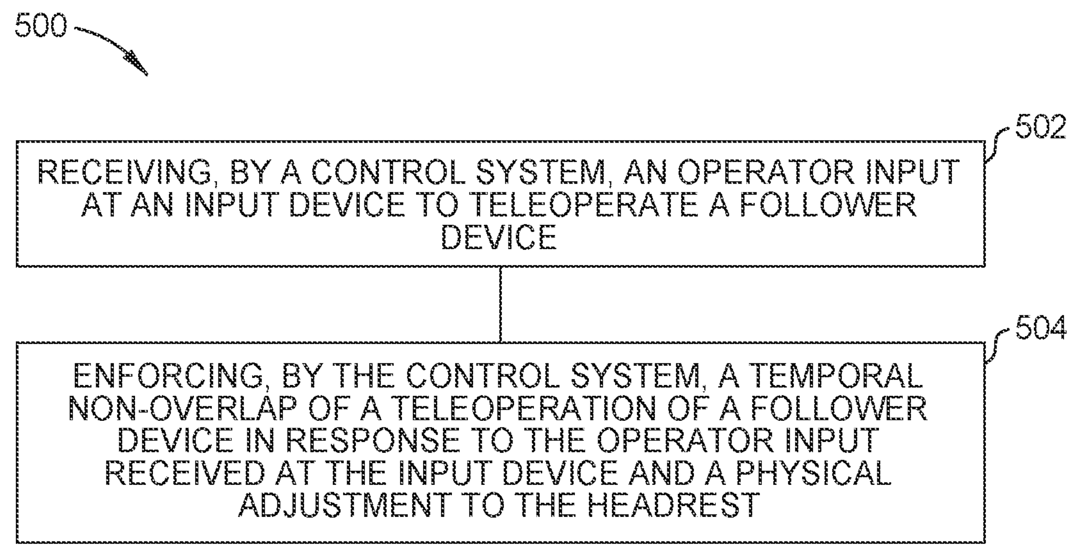
FIG. 5 is a flow diagram of a method for operating a computer-assisted device, the method including enforcing temporal non-overlap of teleoperation of a follower device in response to operator input received at an operator input device and a physical adjustment to a headrest, according to various embodiments.

FIG. 5 is a flow diagram of a method 500 for operating a computer-assisted device, such as the teleoperated system 100 described above, or other similar system. The method 500 enforces a temporal non-overlap of (i) teleoperation of a follower device in response to operator input received at an operator input device, and (ii) a physical adjustment of a headrest, according to various embodiments. In this manner, the computer-assisted device cannot inadvertently command operation of a follower device while physically adjusting the headrest, which improves system performance. The method 500 may be stored as instructions, for example in the form of non-transitory, tangible, machine readable media that include executable code, that when run by one or more processors (e.g., processor 150) of the control system 140, causes the teleoperated system 100 to perform the method 500. Some common forms of machine readable media in which the instructions for the method 500 may be stored may include, but are not limited to, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

The method 500 begins at operation 502 by the control system 140 receiving an operator input at an input device 106 to teleoperate a follower device 104.

At operation 504, the control system 140 enforces a temporal non-overlap of (i) a teleoperation of a follower device 104 in response to the operator input received at the input device 106, and (ii) a physical adjustment to a headrest 242. Enforcement at operation 504 of the temporal non-overlap of teleoperation of a follower device 104 and physical adjustment to a headrest 242 may occur independent of any modes that the teleoperated system 100 is currently operating in. In one example, the enforcement at operation 504 may occur while the control system 140 is operating in at least both a teleoperation mode and a headrest adjustment mode. In another example, the enforcement at operation 504 may occur while the control system 140 is operating in only one of a teleoperation mode and a headrest adjustment mode.

In one example, the control system 140 is configured to enforce the temporal non-overlap by causing inhibition of the physical adjustment to the headrest 242 while the control system 140 is commanding the teleoperation of the follower device 104 in response to the operator input. The control system 140 can cause the inhibition of the physical adjustment of the headrest 242 by not issuing a command to a headrest actuator 316 to move the headrest 242, issuing a command to the headrest actuator 316 to maintain the current position of the headrest 242, disabling generation of the headrest 242 motion control within the control software executed by the control system 140, physically locking the position of the headrest 242 (for example by applying a brake to the motion controls of the headrest 242 such as the repositionable structure 340 and/or headrest actuator 316), or by another suitable technique.

In another example, the control system 140 is configured to enforce the temporal non-overlap by not commanding the teleoperation of the follower device 104 in response to the operator input while a physical adjustment to the headrest 242 is occurring. For example, the control system 140 may not command teleoperation of the follower device 104 while a physical adjustment of the headrest 242 is occurring by not issuing a command to a follower device 104, issuing a command to the follower device 104 to maintain the current position or state of the follower device 104, disabling generation of the follower device 104 motion control within the control software executed by the control system 140, physically locking the position or state of the follower device 104 (for example by applying a brake to the motion controls of the follower device 104), or by another suitable technique.

Optionally, if a command for teleoperation of the follower device 104 is not provided while a physical adjustment of the headrest 242 is occurring due to the enforcement at operation 504, the control system 140 may issue a flag to the operator. The flag may be an audible communication, a visual communication, or a tactile communication through the input device 106 and/or headrest 242 242.

In some implementations, when a command for teleoperation of the follower device 104 in response to operator input provided to the input device 106 is not provided because a physical adjustment of the headrest 242 is occurring due to the enforcement at operation 504, the control system 140 may sequentially terminate (i) physical adjustment of the headrest 242, and (ii) if operator input is still being provided to the input device 106, command teleoperation of the follower device 104 based on the operator input currently received by the control system 140 through the input device 106.

Figure 6:
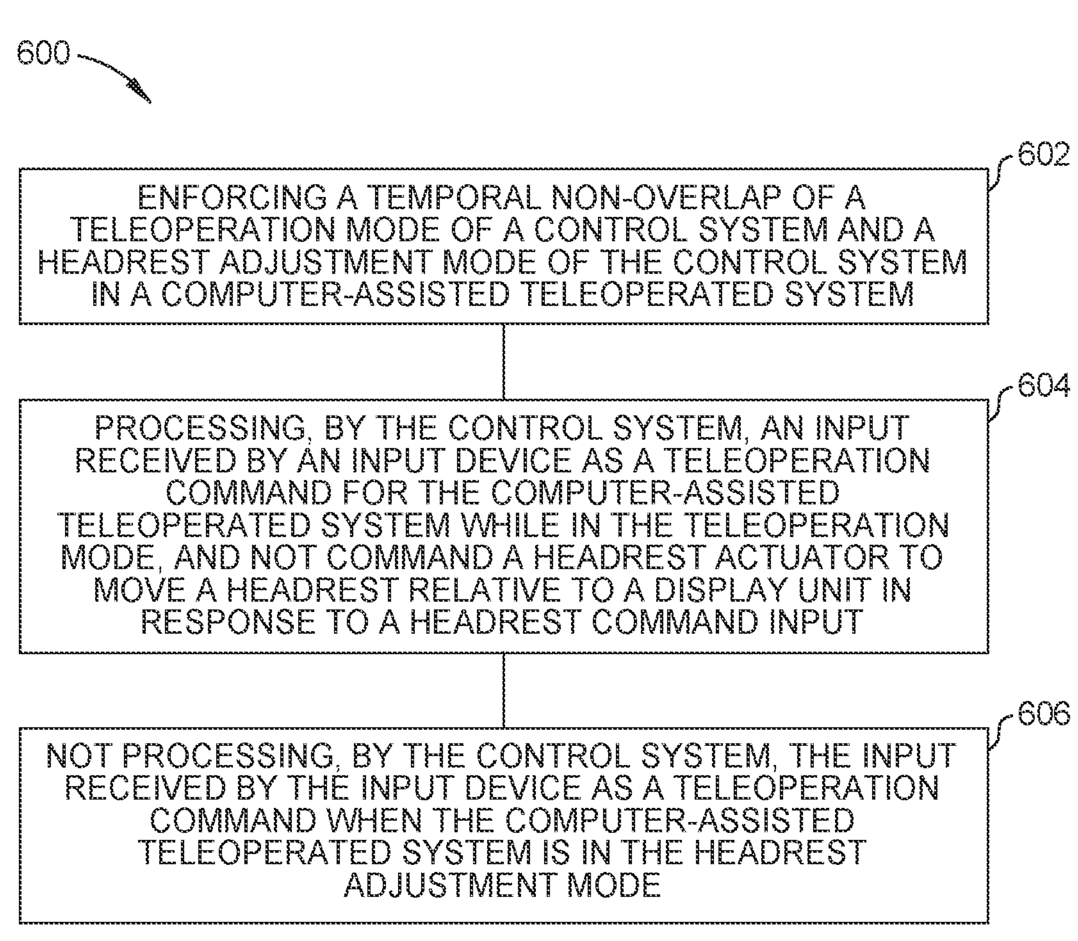
FIG. 6 is a flow diagram of a method for operating a computer-assisted device, the method including enforcing temporal non-overlap of a teleoperation mode and a headrest adjustment mode of a control system of the computer-assisted device, according to various embodiments.

FIG. 6 is a flow diagram of a method 600 for operating a computer-assisted device, such as the teleoperated system 100 described above, or other similar system. The method 600 enforces a temporal non-overlap of a teleoperation mode and a headrest adjustment mode by a control system of the computer-assisted device. In this manner, the computer-assisted device cannot inadvertently be placed in both the teleoperation and a headrest adjustment modes, which improves system performance. The method 600 may be utilized to execute operation 504 of the method 500 described above. Similar to the method 500, the method 600 may be stored as instructions, for example in the form of non-transitory, tangible, machine readable media that include executable code, that when run by one or more processors (e.g., processor 150) of the control system 140, causes the teleoperated system 100 to perform the method 600.

The method 600 begins at operation 602 by enforcing a temporal non-overlap of a teleoperation mode of a control system 140 and a headrest adjustment mode of the control system 140 in a teleoperated system 100. The temporal non-overlap between the teleoperation and headrest adjustment modes is enforced by operation of the control system 140 of the teleoperated system 100.

For example, if the teleoperated system 100 is operating in a teleoperation mode, the control system 140 prevents entry into a headrest adjustment mode. If a command is received by the control system 140 to enter the headrest adjustment mode while in the teleoperation mode, the control system 140 prevents entry into the headrest adjustment mode while the teleoperated system 100 remains in the teleoperation mode. If a command is received to enter the headrest adjustment mode while in the teleoperated system 100 is operating the teleoperation mode, the control system 140 will only allow entry into the headrest adjustment mode once the teleoperated system 100 has exited the teleoperation mode. In some examples, the control system 140 will only allow switching from the teleoperation mode to the headrest adjustment mode once additional criteria is satisfied utilizing information provided by the sensor system 270.

In another example, if the teleoperated system 100 is operating in a headrest adjustment mode, the control system 140 prevents entry into a teleoperation mode. If a command is received by the control system 140 to enter the teleoperation mode while in the headrest adjustment mode, the control system 140 prevents entry into the teleoperation mode while the teleoperated system 100 remains in the headrest adjustment mode. If a command is received to enter the teleoperation mode while in the teleoperated system 100 is operating the headrest adjustment mode, the control system 140 will only allow entry into the teleoperation mode once the teleoperated system 100 has exited the headrest adjustment mode. In some examples, the control system 140 will only allow switching from the headrest adjustment mode to the teleoperation mode once additional criteria is satisfied utilizing information provided by the sensor system 270.

Some additional non-limiting examples of operation 602 are described in greater detail below with reference to a method 700 for enforcing a temporal non-overlap of a teleoperation mode and a headrest adjustment mode.

Continuing to refer to FIG. 6, at operation 604, the control system 140 processes an operator input received at an input device 106 as a teleoperation command for the computer-assisted teleoperated system 100 while in the teleoperation mode, and not command a headrest actuator 316 to move a headrest 242 relative to a display unit 206 in response to a headrest command input. For example, while in the teleoperation mode, the operator 108 may provide input to the input devices 106 which is provided to the control system 140. The operator 108 can, by manipulating the leader input devices 106 of the operator input system 102, cause the control system 140 to command the follower devices 104 to perform various tasks. In a medical example, the follower device 104 can be located near an operating table (e.g., a table, bed, or other support) on which a patient can be positioned. The teleoperated follower device 104 controls the motion and/or function of the instrument 126 teleoperated follower device 104 so as to cause the instrument 126 to perform a task, such as but not limited to, translating, rotating, bending one or more end effectors of the instrument 126, obtaining an image, clamping, cutting, cauterizing, grasping, suturing, stapling, retracting, and suctioning, among other functions.

While the control system 140 is providing teleoperation commands while in the teleoperation mode at operation 604, operation 602 prevents the computer-assisted teleoperated system 100 from moving the headrest 242 relative to the display unit 206 in response to a headrest command input.

At operation 606, the control system 140 would not process the operator input received at the input device 106 as a teleoperation command when the computer-assisted teleoperated system 100 is in the headrest adjustment mode. At operation 606, the control system 140 would command the headrest actuator 316 to move the headrest 242 relative to the display unit 206 in response to the headrest command input. For example, one of the sensors of the sensor system 270 may provide information to the control system 140 indicating that the headrest 242 should be moved, which results in a headrest command that causes the control system 140 to command the headrest actuator 316 to move the headrest 242.

The control system 140 may command the headrest 242 to move in one, two, three, four, five or more DOFs. In one example, the headrest 242 may be moved relative to the housing 250 utilizing the actuator 316. In another example, the headrest 242 may be moved relative to the operator 108 by moving the housing 250 while the headrest 242 remains stationary relative to the housing 250. In another example, the headrest 242 may be moved relative to the operator 108 by moving the housing 250 while the headrest 242 also moves relative to the housing 250. In another example, the headrest 242 may be moved relative to the lenses 223

While the control system 140 is providing commands to move the headrest adjustment in the headrest adjustment mode at operation 606, operation 602 prevents the computer-assisted teleoperated system 100 from providing commands to the teleoperated follower device 104 in response to operator inputs provided to the input devices 106.

Figure 7:
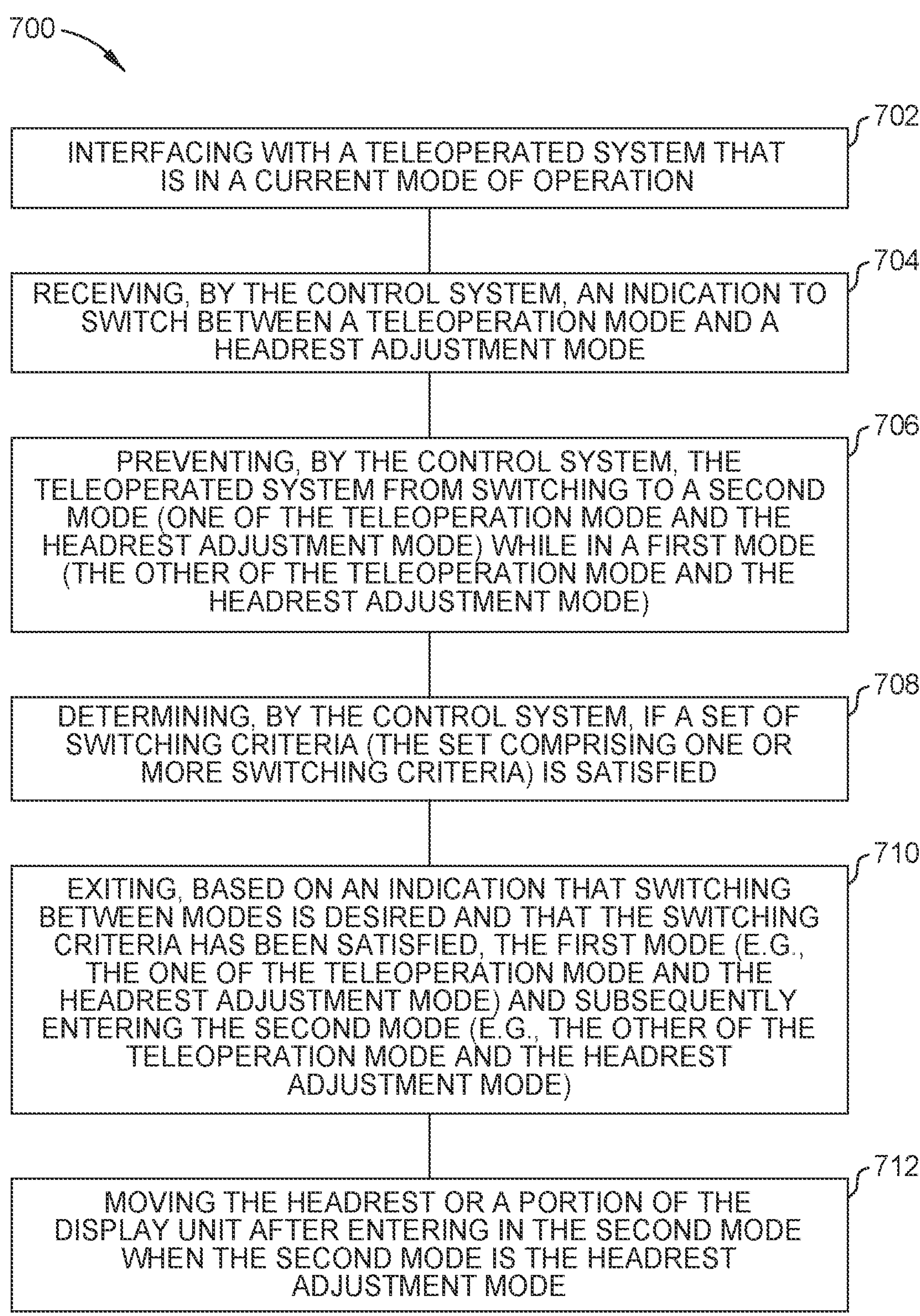
FIG. 7 is a flow diagram of a method for enforcing temporal non-overlap of a teleoperation mode and a headrest adjustment mode of a control system of a computer-assisted device, according to various embodiments.

FIG. 7 is a flow diagram of a method 700 for enforcing a temporal non-overlap of a teleoperation mode and a headrest adjustment mode of a control system of a computer-assisted device. The method 700 may be utilized to execute operation 602 of the method 600 described above. Similar to the methods 500 and 600, the method 700 may be stored as instructions, for example in the form of non-transitory, tangible, machine readable media that include executable code, that when run by one or more processors (e.g., processor 150) of the control system 140, causes the teleoperated system 100 to perform the method 700.

The method 700 begins at operation 702 where the teleoperated system 100 is in a current mode of operation. For example, the teleoperated system 100 may be configured with only a teleoperation mode and a headrest adjustment mode, or configured with one or more modes in addition to teleoperation and headrest adjustment modes. Example other modes include the steerable viewer mode as described above, a fault mode where the teleoperated system has faulted and the pose of the follower device 104 held by brakes or actuators, a power saving mode where one or more parts of the teleoperated system 100 is in low power mode, an idle mode where one or more parts of the teleoperated system 100 is not actively commanded by the control system 140, an follower external manipulation mode where the follower device 104 can be manipulated, a leader clutch mode where one or more leader input device 106 can be moved without commanding teleoperated motion of the follower device 104, and a position hold mode where the pose of the follower device 104 is commanded to be held.

While performing the method 700, the control system 140 prevents the teleoperated system 100 being in both the teleoperation mode and the headrest adjustment mode at the same time. The control system 140 may also prevent the teleoperated system 100 from having temporal overlap of the teleoperation mode with one or more other modes, or allow temporal overlap of the teleoperation mode with one or more other modes. For example, the control system 140 may not allow the teleoperated system 100 to be in the teleoperation mode and the follower external manipulation mode at the same time. As another example, the control system 140 may allow the teleoperated system 100 to be in the teleoperation mode and a steerable viewer mode at the same time, and may even use the motion of the display unit 112 for teleoperation commands.

While performing the method 700, the control system 140 may also prevent the teleoperated system 100 from having temporal overlap of the headrest adjustment mode with one or more other modes, or allow temporal overlap of the headrest adjustment mode with one or more other modes. For example, the control system 140 may allow the teleoperated system 100 to be in the headrest adjustment mode and the steerable viewer mode at the same time, and the operator 108 can easily move the display unit 206 as well as the headrest 242. As another example, control system 140 may allow the teleoperated system 100 to be in the headrest adjustment mode and the external manipulation mode at the same time, such that headrest adjustment can occur simultaneously with configuration changes to the follower device 104.

At operation 704, the control system 140 receives an indication to switch between the teleoperation mode and the headrest adjustment mode. In a first example when the teleoperated system 100 is in the teleoperation mode, the control system 140 may receive an indication to switch to the headrest adjustment mode.

The indication to switch to the headrest adjustment mode may be determined using system operation data, sensor data from one or more sensors of the sensor system 270, and/or operator input by the operator 108 provided through one or more of the input devices 106, 107*a*, 107*b*. Example indicia to switch to the headrest adjustment mode sensed by sensor system 270 may include one or more of a force and/or torque applied to hand controls 114, headrest 242 and/or display unit 206. The indicia to switch to the headrest adjustment mode sensed by sensor system 270 may also include (i) a detection of a gaze, a gaze direction, and/or a change in the gaze of the operator 108, (ii) a change in the distance 304 of the operator 108 or operator's eyes 302 to the lenses 223, display device 360, and/or other part of display unit 206, and/or (iii) a change in a distance of the head of the operator to the headrest 242 and/or display unit 206. The indicia to switch to the headrest adjustment mode sensed by sensor system 270 may also include sensing (i) an absence of the operator 108, (ii) a presence of the operator 108, and/or (iii) movement the head of the operator 108 toward or away of from the display unit 206. As a further example, the indicia to switch to the headrest adjustment mode may also be manually selected by the operator 108 from a digital menu displayed on the display device 360.

In a second example when the teleoperated system 100 is in the headrest adjustment mode, the control system 140 may receive an indication to switch to the teleoperation mode. The indication to switch to the teleoperation mode may be determined using one or more sensors of the sensor system 270, and/or via an operator input by the operator 108 provided through one or more of the input devices 106, 107*a*, 107*b*. The indicia to switch to the teleoperation mode may also be manually selected by the operator 108 from a digital menu displayed on the display device 360. The indicia to switch to the teleoperation mode may also be determined by the control system 140 by the expiration of a predetermined period of time after the last headrest adjustment is made or commanded by the control system 140. The value for the predetermined time period may be stored in memory 160 of the control system 140, selected manually, determined by the control system 140 through machine learning techniques, or selected or retrieved by the control system 140 via another technique.

At operation 706, the control system 140 prevents the teleoperated system 100 from switching to a second mode (one of the teleoperation mode and the headrest adjustment mode) while in a first mode (the other of the teleoperation mode and the headrest adjustment mode). More specifically, when the control system 140 receives an indicia to change modes at operation 704, the control system 140 performs operations 708, 710 before switching modes. If the control system 140 receives an indicia to change modes at operation 704, and has determined that the teleoperated system 100 is in neither of the teleoperation nor headrest adjustment mode, operation 708 may be skipped and the method 700 proceed directly to operation 712.

At operation 708, the control system 140 determines if a set of switching criteria (the set comprising one or more switching criteria) is met (that is, determined to have been satisfied). To determine if the set of switching criteria has been satisfied, one or more switching criteria of the set are compared against information obtained from the teleoperated system 100 (e.g., mode of operation, etc.) or obtained from one or more of the sensors of the sensor system 270. Switching criteria may be stored in memory 160 of the control system 140, selected or input manually, determined by the control system 140 through machine learning techniques, or selected or retrieved by the control system 140 via another technique.

In one example, the set of switching criteria is satisfied when the control system 140 determines that, in response to receiving an indication to enter the headrest adjustment mode, the control system 140 is not in the teleoperation mode. In various examples, the set of switching criteria contain different individual criterion, and determining that the set of switching criteria has been satisfied comprises determining the satisfaction of the individual criterion. In an example, a criterion of the set of switching criteria is satisfied when a force or a torque applied to the headrest 242 and/or display unit 206 is determined to exceed a predetermined amount. The predetermined amount may be stored in memory 160 of the control system 140, selected manually, determined by the control system 140 through machine learning techniques, or selected or retrieved by the control system 140 via another technique. In another example, a criterion of the set of switching criteria is satisfied when a temporal history of a force and/or torque applied to the headrest is determined to be consistent with at least one operator interaction selected from the group consisting of: (i) pulling then pushing on the headrest; (ii) tapping on the headrest; (iii) wiggling the headrest; (iv) twisting the headrest; (v) and pushing on the headrest for longer than a predetermined duration. In another example, a criterion of the set of switching criteria is satisfied when sensor signals indicative of the operator interactions with the headrest are determined to be performed with a body part other than a head of the operator. In another example, a criterion of the set of switching criteria is satisfied when (i) information provided by the sensors to the control system 140 meets switching criteria stored in the memory 160 of the control system 140; (ii) that the operator 108 is engaged with the operator input system 102; (iii) that a hand of the operator 108 is engaged with the display unit 206; (iv) that a head of the operator 108 is engaged with the display unit 206; (v) that a gaze of the operator 108 is directed toward an image displayed by the display unit 206; (vi) that the control system 140 is in a manual adjustment mode; and/or (vii) that the control system 140 is in a headrest adjustment mode. In another example, a criterion of the set of switching criteria is satisfied when (i) the control system is in a manual adjustment mode; (ii) a geometric parameter is determined to indicate that an optical relationship between an eye of the operator and an image displayed by the display unit is outside a target optical relationship; and/or (iii) a position of an eye of the operator relative to a position or orientation of the display unit is outside a target physical relationship.

In yet another example, the set of switching criteria is satisfied when the control system 140 determines that, in response to receiving an indication to enter a second mode (one of the teleoperation mode and the headrest adjustment mode) while in a first mode (the other of the teleoperation mode and the headrest adjustment mode), the control system 140 determines that the second mode has priority over the first mode. Priority of one mode over the another mode may be set as a control parameter stored in memory 160 of the control system 140, selected manually, determined by the control system 140 through machine learning techniques, or selected or retrieved by the control system 140 via another technique. Based on the control system 140 determining that the second mode has priority over the first mode, operation 708 is satisfied and the method proceeds to operation 710. Conversely, based on the control system 140 determining that the first mode has priority over the second mode, operation 708 is not satisfied, operations 710 and 712 are not performed. When operations 710 and 712 are not performed, the control system 140 may generate a flag to alert the operator 108. The flag may be an audible communication, a visual communication, or a tactile communication through the input device 106 and/or headrest 242 242.

At operation 710, the control system 140, based on an indication that switching between modes is desired and that the switching criteria has been satisfied, exits the first mode (e.g., the one of the teleoperation mode and the headrest adjustment mode) and subsequently enters the second mode (e.g., the other of the teleoperation mode and the headrest adjustment mode). In a first example, in response to receiving an indication to exit the teleoperation mode while in the headrest adjustment mode at operation 704, and determining that the switching criteria has been satisfied at operation 708, the control system 140 causes the teleoperated system 100 to exit the teleoperation mode and enter the headrest adjustment mode. In a second example, in response to receiving an indication to exit the headrest adjustment mode while in the headrest adjustment mode at operation 704, and determining that the switching criteria has been satisfied at operation 708, the control system 140 causes the teleoperated system 100 to exit the headrest adjustment mode and enter the teleoperation mode.

If the headrest adjustment mode has been entered, the teleoperated system 100 is in a mode where the control system 140 would command a headrest actuator 316 to move the headrest 242 relative to a display unit 206 in response to a headrest command input at operation 712. The headrest command input is provided to the control system 140 using sensor data from one or more the sensors of the sensor system 270. The headrest command input may be a directly sensed or indirectly derived force and/or torque applied to one or more of the headrest 242, the hand controls 114, the display unit 206, etc. The headrest command input may be a position, orientation, or motion of the head of an operator 108 detected by one or more the sensors of the sensor system 270. The headrest command input may be a detected gaze of an operator 108, distance and/or orientation of the eyes 302 of the operator 108 relative to a position or orientation of the display unit 206 or display device 360 or image displayed by the display device 360 (e.g., being determined to be outside a target or optical physical relationship), based on sensor data from one or more the sensors of the sensor system 270.

At operation 712, the headrest 242 may be moved manually by the operator 108, and/or automatically by the control system 140. The headrest 242 may be moved in any of the manners described above, or moved using another suitable technique. For example, headrest 242 may be moved relative to the display unit 206 and/or the lenses 223, or alternatively, moved with the display unit 206 and/or the lenses 223 in a common frame. At operation 712, the headrest 242 may be moved to place the headrest 242 and/or lenses 223 in a predefined target position that improves the quality images as viewed by the operator 108 on the display device 360, and/or reduces operator fatigue.

Alternatively at operation 712, when the headrest adjustment mode has been entered, the control system 140 may move a portion of the display unit 206 in response to a command input.

Advantageously, the disclosed techniques enforce a temporal non-overlap of the teleoperation mode and the headrest adjustment mode of a teleoperation system 100. The temporal non-overlap prevents undesired motion of the headrest while the teleoperated system is in the teleoperation mode. The temporal non-overlap also prevents inadvertent motion of follower devices while the teleoperated system is in the headrest adjustment mode. Additionally, inadvertent motion of the headrest is prevented during the teleoperation mode, thus mitigating inadvertent head movement that potentially could detrimentally affect the results during teleoperation. Moreover, allowing the headrest of a display unit to be repositioned while in the headrest adjustment mode allows an operator to more comfortably use the teleoperated system, thus reducing operator fatigue. Furthermore, repositioning the headrest may improve the quality of images as viewed by the operator, thus allowing more precise and high-quality work to be performed by using the teleoperated system.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and, in a manner, consistent with the scope of the embodiments disclosed herein.

What is claimed is:

1. A computer-assisted teleoperation system comprising:

an input device configured to receive operator inputs from an operator;

a display unit configured to display images viewable by the operator;

a headrest coupled to the display unit, the headrest configured to be contacted by a head of the operator; and a control system communicatively coupled to the input device, the control system comprising one or more processors, wherein the control system is configured to:

enforce a temporal non-overlap between a physical adjustment to the headrest during a headrest adjustment mode and a teleoperation of a follower device during a teleoperation mode in response to the operator input received at the input device by preventing the control system from entering the headrest adjustment mode in response to receiving an indication to enter the headrest adjustment mode while the control system remains in the teleoperation mode.

2. The computer-assisted teleoperation system of claim 1, wherein the control system is configured to enforce the temporal non-overlap by:

while the control system is commanding the teleoperation of the follower device in response to the operator input, causing inhibition of the physical adjustment to the headrest; or while the physical adjustment to the headrest is occurring, not commanding the teleoperation of the follower device in response to the operator input.

3. The computer-assisted teleoperation system of claim 1, wherein:

while in the teleoperation mode, the control system is further configured to process an input received at the input device as a teleoperation command for the follower device, and to cause inhibition of the physical adjustment of the headrest relative to the display unit in response to a headrest command input; and while in the headrest adjustment mode, the control system is further configured to not process the input received at the input device as the teleoperation command, and to not cause inhibition of the physical adjustment of the headrest relative to the display unit in response to the headrest command input.

4. The computer-assisted teleoperation system of claim 3, wherein the control system is configured to enforce the temporal non-overlap by:

in response to receiving an indication to enter the teleoperation mode while the control system is in the headrest adjustment mode, causing the control system to exit the headrest adjustment mode and then enter the teleoperation mode.

5. The computer-assisted teleoperation system of claim 3, wherein the control system is configured to enforce the temporal non-overlap by:

in response to receiving an indication to enter the teleoperation mode, determining that a teleoperation mode criteria set has been satisfied before entering the teleoperation mode, wherein the teleoperation mode criteria set comprises the control system not being in the headrest adjustment mode.

6. The computer-assisted teleoperation system of claim 3, wherein the control system is configured to enforce the temporal non-overlap by:

while the control system is in the headrest adjustment mode, preventing the control system from entering the teleoperation mode in response to receiving an indication to enter the teleoperation mode.

7. The computer-assisted teleoperation system of claim 3, wherein the control system is configured to enforce the temporal non-overlap by:

in response to receiving an indication to enter the headrest adjustment mode while the control system is in the teleoperation mode, causing the control system to exit the teleoperation mode and then enter the headrest adjustment mode.

8. The computer-assisted teleoperation system of claim 3, wherein the control system is configured to enforce the temporal non-overlap by:

in response to receiving an indication to enter the headrest adjustment mode, determining that an adjustment mode criteria set has been satisfied before entering the headrest adjustment mode, wherein:

the adjustment mode criteria set has been satisfied comprises the control system not being in the teleoperation mode.

9. The computer-assisted teleoperation system of claim 8, wherein the adjustment mode criteria set has been satisfied further comprises:

a force or a torque applied to the headrest being determined to exceed a predetermined amount.

10. The computer-assisted teleoperation system of claim 8, wherein the adjustment mode criteria set has been satisfied further comprises:

a temporal history of a force or torque applied to the headrest being determined to be consistent with at least one operator interaction selected from the group consisting of: pulling then pushing on the headrest, tapping on the headrest, wiggling the headrest, twisting the headrest, and pushing on the headrest for longer than a predetermined duration.

11. The computer-assisted teleoperation system of claim 8, further comprising:

a sensor system configured to detect operator interactions with the headrest, and to provide sensor signals indicative of the operator interactions with the headrest;

wherein the adjustment mode criteria set has been satisfied further comprises the operator interactions with the headrest being determined to be performed with a body part other than a head of the operator.

12. The computer-assisted teleoperation system of claim 11, wherein the body part comprises a hand.

13. The computer-assisted teleoperation system of claim 11, wherein the control system is configured to determine that the operator interactions with the headrest performed with the body part other than the head by:

determining that a temporal history of force or torque applied to the headrest is inconsistent with head interaction; or determining that the temporal history of the force or the torque applied to the headrest is consistent with hand interaction.

14. The computer-assisted teleoperation system of claim 8, wherein the adjustment mode criteria set has been satisfied further comprises:

the operator being determined to be not engaged with the input device;

a hand of the operator being determined to be engaged with the display unit;

the head of the operator being determined to be engaged with the display unit; or a gaze of the operator being determined to be directed toward an image displayed by the display unit.

15. The computer-assisted teleoperation system of claim 8, wherein the adjustment mode criteria set has been satisfied further comprises:

the control system being in a manual adjustment mode.

16. The computer-assisted teleoperation system of claim 8, wherein the adjustment mode criteria set has been satisfied further comprises:

a geometric parameter is determined to indicate that an optical relationship between an eye of the operator and an image displayed by the display unit is outside a target optical relationship.

17. The computer-assisted teleoperation system of claim 8, wherein the adjustment mode criteria set further comprises:

a position of an eye of the operator relative to a position or orientation of the display unit is outside a target physical relationship.

18. The computer-assisted teleoperation system of claim 3, further comprising:

a headrest actuator operable to move the headrest relative to the display unit in more than one spatial degree of freedom; and the control system is further configured to, while in the headrest adjustment mode, command the headrest actuator to constrain the headrest to move in a single spatial degree of freedom.

19. The computer-assisted teleoperation system of claim 3, wherein:

the computer-assisted teleoperation system further comprises: a headrest actuator operable to move the headrest relative to the display unit, and a repositionable structure coupled to the display unit, the repositionable structure operable to control motion of the display unit in space; and the control system is further configured to: while the control system is in the headrest adjustment mode, command the headrest actuator to maintain a position of the headrest in a common frame while the control system commands the repositionable structure to move the display unit relative to the common frame.

20. The computer-assisted teleoperation system of claim 3, wherein:

the computer-assisted teleoperation system further comprises: a headrest actuator operable to move the headrest relative to the display unit, and a repositionable structure coupled to the display unit, the repositionable structure operable to control motion of the display unit in space; and the control system is further configured to: while the control system is in the headrest adjustment mode, command the headrest actuator to change a position of the headrest in a common frame of reference while the control system commands the repositionable structure to maintain a position of the display unit in the common frame.

21. The computer-assisted teleoperation system of claim 3, wherein:

the computer-assisted teleoperation system further comprises: a headrest actuator operable to move the headrest relative to the display unit; and the control system is further configured to: while the control system is in the headrest adjustment mode, command the headrest actuator to move the headrest relative to the display unit in a direction corresponding to a direction of a force or torque applied to the headrest.

22. The computer-assisted teleoperation system of claim 3, further comprising:

a headrest actuator operable to move the headrest relative to the display unit;

a sensor system configured to detect a motion of a head of the operator; and wherein the control system is further configured to:

while the control system is in the headrest adjustment mode, command the headrest actuator to cause the headrest to follow a motion of a head of the operator.

23. The computer-assisted teleoperation system of claim 3, wherein the control system is further configured to:

in response to receiving an indication to exit the teleoperation mode while in the teleoperation mode, cause the control system to exit the teleoperation mode and enter the headrest adjustment mode.

24. A method for operating a computer-assisted teleoperation system comprising an input device configured to receive operator inputs from an operator, a display unit configured to display images viewable by the operator, a headrest coupled to the display unit, and a control system comprising one or more processors, the method comprising:

receiving, by the control system, an operator input at the input device to teleoperate a follower device; and enforcing, by the control system, a temporal non-overlap between a physical adjustment to the headrest during a headrest adjustment mode and a teleoperation of a follower device during a teleoperation mode in response to the operator input received at the input device by preventing the control system from entering the headrest adjustment mode in response to receiving an indication to enter the headrest adjustment mode while the control system remains in the teleoperation mode.

* * * * *